United States Patent [19]

Kool

[11] Patent Number: 5,714,320
[45] Date of Patent: Feb. 3, 1998

[54] ROLLING CIRCLE SYNTHESIS OF OLIGONUCLEOTIDES AND AMPLIFICATION OF SELECT RANDOMIZED CIRCULAR OLIGONUCLEOTIDES

[75] Inventor: Eric T. Kool, Rochester, N.Y.

[73] Assignee: University of Rochester, Rochester, N.Y.

[21] Appl. No.: 393,439

[22] Filed: Feb. 23, 1995

Related U.S. Application Data

[63] Continuation-in-part of Ser. No. 47,860, Apr. 15, 1993, abandoned.

[51] Int. Cl.$^6$ .............................. C12Q 1/68; C12Q 1/70; C12P 19/34; C07H 21/04
[52] U.S. Cl. .............................. 435/6; 435/5; 435/91.2; 435/91.1; 536/24.5; 536/24.3; 536/24.32; 536/24.33; 536/23.1
[58] Field of Search ......................... 435/6, 5, 91.1, 435/91.2; 514/44; 536/24.5, 24.3–24.33, 23.1

[56] References Cited

U.S. PATENT DOCUMENTS

| 4,795,700 | 1/1989 | Dervan et al. | 435/5 |
| 4,837,312 | 6/1989 | Dervan et al. | 536/27 |
| 5,258,506 | 11/1993 | Urdea et al. | 536/23.1 |
| 5,354,668 | 10/1994 | Auerbach | 435/6 |
| 5,470,724 | 11/1995 | Ahern | 435/91.2 |
| 5,498,531 | 3/1996 | Jarrell et al. | 435/91.31 |
| 5,500,357 | 3/1996 | Taira et al. | 435/91.31 |

FOREIGN PATENT DOCUMENTS

| 4-304900 | 10/1992 | Japan | C12Q 1/68 |
| 5-146299 | 6/1993 | Japan | C12Q 1/68 |
| WO 92/17484 | 10/1992 | WIPO | |

OTHER PUBLICATIONS

James, Antiviral Chemistry and Chemotherapy 2: 191–214, 1991.
Gura, Science 270: 575–577, 1995.
Fire and Xu, PNAS 92:4641–4645, 1995.
Prakash and Kool, J. Am. Chem. Society 114:3523–3527, 1992.
Daube and Hippel, Science 258: 1320–1324, 1992.
Daubendiek et al. J. Am. Chem Society 117:7818–7819, 1995.
Cwirla et al. PNAS 87: 6378–6382, 1990.
*Affinity Chromatography: Practical & Theoretical Aspects*; Ed: P. Mohr; Dekker Publishing; New York (1985); Title page, Copyright page, and Contents pages (pp. v–viii).
G.W. Ashley et al., "Chemical Synthesis of Oligodeoxynucleotide Dumbbells", *Biochemistry*, 30, 2927 (1991).

(List continued on next page.)

*Primary Examiner*—W. Gary Jones
*Assistant Examiner*—Dianne Rees
*Attorney, Agent, or Firm*—Mueting, Raasch, Gebhardt & Schwappach, P.A.

[57] ABSTRACT

The present invention provides methods for synthesis, selection, and amplification of DNA and RNA oligonucleotides and analogs. The method for synthesizing an oligonucleotide involves: providing an effective amount of an isolated circular oligonucleotide template which comprises at least one copy of the desired oligonucleotide sequence linked to a cleavage site; providing an effective amount of an isolated oligonucleotide primer; annealing the primer to the circular template to form a primed circular template; and combining the primed circular template with an effective amount of at least two types of nucleotide triphosphates and an effective amount of a polymerase enzyme to form a nucleotide multimer complementary to the circular oligonucleotide template, wherein the nucleotide multimer comprises multiple copies of the oligonucleotide sequence joined end to end. Preferably, the nucleotide multimer is cleaved to produce oligonucleotides having well-defined ends.

47 Claims, 2 Drawing Sheets

OTHER PUBLICATIONS

S.L. Beaucage et al., "Deoxynucleoside Phosphoramidites—A New Class of Key Intermediates for Deoxypolynucleotide Synthesis", *Tetrahedron Lett.*, 22, 1859–1862 (1981).

L.C. Bock et al., "Selection of single–stranded DNA molecules that bind and inhibit human thrombin", *Nature*,355, 564–566 (1992).

J. Chin et al., "Catalytic Hydrolysis of Amides at Neutral pH", *J. Chem. Soc., Chem. Commun.*, 1326–1328 (1990).

J. Compton, "Nucleic acid sequence–based amplification", *Nature*, 350, 91–92 (1991).

David D'Souza and Eric Kool, "Strong Binding of Single–stranded DNA by Stem–Loop Oligonucleotides", *J. Biomolecular Structure and Dynamics*, 10, 141–152 (1992).

Eisenberg et al., *PNAS USA*, 73, 3151 (1976).

A.D. Ellington et al., "In vitro selection of RNA molecules that bind specific ligands", *Nature*, 346, 818–822 (1990).

A.D. Ellington et al., "Selection in vitro of single–stranded DNA molecules that fold into specific ligand–binding structures", *Nature*, 355, 850–852 (1992).

M. Famulok et al., "Streospecific Recognition of Tryptophan Agarose by in vitro Selected RNA", *J. Am. Chem. Soc.*, 114, 3990–3991 (1992).

A.C. Forster et al., "Structural and Ionic Requirements for Self–Cleavage of Virusoid RNAs and trans Self–cleavage of Viroid RNA", *Cold Spring Harbor Symp. Quant. Biol.*, 52, 249–259 (1987).

J. Haseloff et al., "Simple RNA Enzymes with New and Highly Specific Endoribonuclease Activities"*Nature*, 334, 585–591 (1988).

Harshey et al., *Proc. Natl. Acad. Sci. USA*, 78, 1090–1094 (1981).

E. Kanaya et al., "Template–Directed Polymerization of Oligoadenylates Using Cyanogen Bromide", *Biochemistry*, 25, 7423–7430 (1986).

S. Kazakov et al., "A Trinucleotide Can Promote Metal Ion–Dependent Specific Cleavage of RNA", *Proc. Natl. Acad. Sci. USA*, 89, 7939–7943 (1992).

J.H. Kim et al., "Dimethyl Phosphate Hydrolysis at Neutral pH", *J. Am. Chem. Soc.*, 114, 9792–9795 (1992).

I. Kitajima et al., "Ablation of Transplanted TYLV–I Tax–Transformed Tumors in Mice by Antisense Inhibition of NF–kB", *Science*, 258, 1792–1795 (1992).

E. Kool, "Molecular Recognition by Circular Oligonucleotides: Increasing the Selectivity of DNA Binding", *J. Am. Chem. Soc.*, 113, 6265–6266 (1991).

E.T. Kool et al., Abstract of National Institute of Health Grant No. RO1–GM46625.

Kornberg, DNA Replication, W.H. Freeman, San Francisco, p. 569 (1980).

J.F. Milligan et al., "Oligoribonucleotide synthesis using T7 RNA polymerase and synthetic DNA templates", *Nucleic Acids Res.*, 15, 8783 (1987).

Y. Miyamoto et al., "Total Synthesis of (+)–Validoxylamine G", *J. Chem. Soc., Chem. Commun.*, 999–1000 (1990).

New England Biolabs Catalog, ΦX174 (1994).

*Oligodeoxynucleotides: Antisense Inhibitors of Gene Expression*; J.S. Cohen, Ed.; CRC Press: Boca Raton, FL, 1989; Title page, Copyright page, and Contents pages (pp. v–viii).

B.M. Olivera et al., "Enzymic Joining of Polynucleotides: IV. Formation of a Circular Deoxyandenylate–Deoxythymidylate Copolymer", *J. Mol. Biol.*, 36, 275–285 (1968).

D. Pei et al., "A Combinatorial Approach Toward DNA Recognition", *Science*, 253, 1408–1411 (Sep. 1991).

J. Piccirilli et al., "Enzymatic Incorporation of a New Base Pair into DNA and RNA Extends the Genetic Alphabet", *Nature*, 343, 33–37 (1990).

A. Podhadjska et al., "Conversion of the FokI Endonuclease to a Universal Restriction Enzyme: Cleavage of Phage M13mp7 DNA at Predetermined Sites", *Gene*, 40, 175–182 (1985).

G. Prakash et al., "Molecular Recognition by Circular Oligonucleotides. Strong Binding of Single–stranded DNA and RNA", *J. Chem. Soc., Chem. Commun.*, 17, 1161–1163 (1991).

G. Prakash et al., "Structural Effects in the Recognition of DNA by Circular Oligonucleotides", *J. Am. Chem. Soc.*, 114, 3523–3527 (1992).

M.Z. Ratajczak et al., "In vivo treatment of human leukemia in a scid mouse model with c–myb antisense oligodeoxynucleotides", *PNAS*, 89, 11823–11827 (1992).

D.L. Robertson et al., "Selection in vitro of an RNA Enzyme that Specifically Cleaves Single–Stranded DNA", *Nature*, 344, 467–468 (1990).

S. Rumney et al., "DNA Recognition by Hybrid Oligoether–Oligodeoxynucleotide Macrocycles", *Angew. Chem., Intl. Ed. English*, 31, 1617–1619 (1992).

R.K. Saiki et al., "Primer–Directed Enzymatic Amplification of DNA with a Thermostable DNA Polymerase", *Science*, 239, 487–491 (1988).

Sambrook et al., *Molecular Cloning: A Laboratory Guide*; 2nd ed.; Cold Spring Harbor, NY (1989), Title page, Copyright page, Contents pages (pp. v–xxxii) and Chapter 13 (pp. 13.2–13.104).

S.A. Scaringe et al., "Chemical Synthesis of Biologically Active Oligoribonucleotides Using –cyanoethyl Protected Ribonucleoside Phosphoramidites", *Nucleic Acids Res.*, 18, 5433–5441 (1990).

E.S. Simon et al., "Convenient Syntheses of Cytidine 5'–Triphosphate, Guanosine 5'–Triphosphate, and Uridine 5'–Triphosphate and Their Use in the Preparation of UDP–glucose, UDP–glucuronic Acid, and GCP–mannose", *J. Org. Chem.*, 55, 1834–1841 (1990).

"The Single Stranded DNA Phages", D.T. Denhardt et al., Eds., Cold Spring Harbor Press, Cold Spring Harbor, pp. 298–299 (1978). vol. # not applicable.

W. Szybalski et al., "Universal Restriction Endonucleases: Designing Novel Cleavage Specificites Combining Adapter Oligodeoxynucleotide and Enzyme Moieties", *Gene*, 40, 169–173 (1985).

D.C. Tessier et al., "Ligation of Single–Stranded Oligodeoxyribonucleotides by T4 RNA Ligase", *Anal. Biochem.*, 158, 171–178 (1986).

J.Tomizawa et al., "Factor–Independent Termination of Transcription in a Stretch of Deoxyadenosine Residues in the Template DNA", *Cell*, 51 623–630 (1987).

C. Tuerk et al., "Systematic Evoluation of Ligands by Exponential Enrichment: RNA Ligands to Bactgeriophage T4 DNA Polymerase", *Science*, 249, 505–510 (Aug. 1990).

C. Tuerk et al., "RNA Pseudoknots that Inhibit Human Immunodeficiency Virus Type 1 Reverse Transcriptase", *PNAS*, 89, 6988–6992 (1992).

E. Uhlmann et al., "Antisense Oligonucleotides: A New Therapeutic Principle", *Chem. Rev.*, 90, 543–584 (1990).

Y. Vaishnav et al., "The Biochemistry of AIDS", *Ann. Rev. Biochem.*, 60, 577–630 (1991).

G.T. Walker et al., "Isothermal in vitro amplification of DNA by a restriction enzyme/DNA polymerase system", *PNAS*, 89, 392–396 (1992).

Watson, "Molecular Biology of the Gene", W.A. Benjamin, Inc., 238–241 (1976) vol. # not applicable.

Luis Blanco, et al., "Highly Efficient DNA Synthesis by the Phage o29 DNA Polymerase", *J. Biol. Chem.*, 264, 8935–8940, (1989).

Hyeon–Sook Koo, et al., "Determination of the Extent of DNA Bending by an Adenine–Thymine Tract", *Biochemistry*, 29, 4227–4234, (1990).

Levy Ulanovsky, et al., "Curved DNA: Design, Synthesis and Circularization", *PNAS USA*, 83, 862–866, (1986).

5,714,320

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AAAGAAGAGG GAAGAAAGAA AAGGGGTGGA AAAG    34

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTTTCCACCC CTTTCTTTC TTCCCTCTTC TTTC    34

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GAAAGAAGAG  GGAAGAAAGA  AAAGGGGTGG  AAAA                                34
```

( 2 ) INFORMATION FOR SEQ ID NO:4:

( i ) SEQUENCE CHARACTERISTICS:
        ( A ) LENGTH: 204 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TTTCCACCC  CTTTTCTTTC  TTCCTCTTC  TTTCTTTTCC  ACCCCTTTTC  TTTCTTCCCT      60

CTTCTTTCTT  TTCCACCCCT  TTTCTTTCTT  CCCTCTTCTT  TCTTTTCCAC  CCCTTTTCTT   120

TCTTCCCTCT  TCTTTCTTTT  CCACCCCTTT  TCTTTCTTCC  CTCTTCTTTC  TTTTCCACCC   180

CTTTTCTTTC  TTCCCTCTTC  TTTC                                            204
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CAAAAAAAAA  AAACAAAAAA  AAAAAA                                           26
```

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GTTTTTTTTT  TTTGTTTTTT  TTTTTTGTTT  TTTTTTTT                             39
```

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
TTTTTTTTT TT                                                                     12
```

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
AAGAAAGAAA AG                                                                    12
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:9:

```
CTTAGAGACG AAGATCAAAC GTCTCTAAGA CTTTCTTT                                        39
```

( 2 ) INFORMATION FOR SEQ ID NO:10:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
TCTTAGAGAC GTTTGATCTT CGTCTCTAAG AAAGAAAAGT CTTAGAGACG TTTGATCTTC                60
GTCTCTAAGA AAGAAAAGTC TTAGAGACGT TGATCTTCG TCTCTAAGAA AGAAAAG                    117
```

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:11:

```
AAGAAAGAAA AG                                                                    12
```

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
TCTTAGAGAC GTTTGATCTT CGTCTCT                                                    27
```

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GATCAGAAAA GAAAGAAGGA GGAAGAAAGA AAAG                              34

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:14:

GAAAAGAAAG AAGGAGGAAG AAAGAAAAGG ATCA                              34

( 2 ) INFORMATION FOR SEQ ID NO:15:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GATCCTTTTC TTTCTTCCTC CTTCTTTCTT TTCTGATCCT TTTC                 44

( 2 ) INFORMATION FOR SEQ ID NO:16:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:16:

TTCTTTCTTT TCTGATCCTT TTCTTTCTTC CTCC                              34

( 2 ) INFORMATION FOR SEQ ID NO:17:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GATCAGAAAA GAAAGAAGGA GGAAGAAAGA AAAGGATCA                       39

( 2 ) INFORMATION FOR SEQ ID NO:18:

( i ) SEQUENCE CHARACTERISTICS:
        ( A ) LENGTH: 34 base pairs
        ( B ) TYPE: nucleic acid (C) STRANDEDNESS: single
    (D) TOPOLOGY: linear ( i i ) MOLECULE TYPE: DNA (genomic)

( x i ) SEQUENCE DESCRIPTION: SEQ ID NO:18:

AAAAGAAAGA AGGAGGAAGA AAGAAAAGGA TCAG    34

( 2 ) INFORMATION FOR SEQ ID NO:19:

( i ) SEQUENCE CHARACTERISTICS:
        (A) LENGTH: 34 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:19:

GATCCTTTTC TTCTTCCTC CTTCTTTCTT TTCT    34

( 2 ) INFORMATION FOR SEQ ID NO:20:

( i ) SEQUENCE CHARACTERISTICS:
        (A) LENGTH: 33 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:20:

CGAGAAAAGA AAGAAGGAGG AAGAAAGAAA AGA    33

( 2 ) INFORMATION FOR SEQ ID NO:21:

( i ) SEQUENCE CHARACTERISTICS:
        (A) LENGTH: 34 base pairs
        (B) TYPE: nucleic acid
        (C) STRANDEDNESS: single
        (D) TOPOLOGY: circular ( i i ) MOLECULE TYPE: DNA (genomic)

( x i ) SEQUENCE DESCRIPTION: SEQ ID NO:21:

GATCTTTTCT TCTTCCTCC TTCTTTCTTT TCTC    34

( 2 ) INFORMATION FOR SEQ ID NO:22:

( i ) SEQUENCE CHARACTERISTICS:
        (A) LENGTH: 39 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:22:

AGACGAAGAT CAAACGTCTC TAAGACTTTT CTTTCTTAG    39

( 2 ) INFORMATION FOR SEQ ID NO:23:

( i ) SEQUENCE CHARACTERISTICS:
        (A) LENGTH: 31 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:23:

AGGNNNNNNN NNNNNNNNNN NNNAAAAAAC C           31

( 2 ) INFORMATION FOR SEQ ID NO:24:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:24:

AAAAACCAG GNNNNNNNNN NNNNNNNNNN N             31

( 2 ) INFORMATION FOR SEQ ID NO:25:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

TGGTTTTTN NNNNNNNNNN NNNNNNNNNC C             31

( 2 ) INFORMATION FOR SEQ ID NO:26:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:26:

TTTTTNNNN NNNNNNNNNN NNNNNCCTG G              31

( 2 ) INFORMATION FOR SEQ ID NO:27:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TTTTCTTTCT T                                   11

( 2 ) INFORMATION FOR SEQ ID NO:28:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:28:

CTTTCTTCTT TCCTTCGATT CCTTCTTCT TTCCTTCGAT TC    42

( 2 ) INFORMATION FOR SEQ ID NO:29:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:29:

```
CTTTCTTCTT  TCCTTTCTC  GATCTTTCC  TTTCTTCTTT  CCTTTTCTCG  ATCTTTC                58
```

( 2 ) INFORMATION FOR SEQ ID NO:30:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:30:

```
CTTTCTTCTT  TCCTTTCTT  TTTCGATTTT  TCTTTTCCTT  TCTTCTTTCC  TTTTCTTTTT           60
CGATTTTTCT  TTTC                                                                74
```

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
AGGAAAGAAG  AAAGGA                                                              16
```

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
TGTTAACTTC  TGCGTCAT                                                            18
```

( 2 ) INFORMATION FOR SEQ ID NO:33:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

```
TCTCTTCGAC  TCTCTCTNNN  NNNNNNNNNN  NNNNNNNTCT  C                               41
```

( 2 ) INFORMATION FOR SEQ ID NO:34:

( i ) SEQUENCE CHARACTERISTICS:

( A ) LENGTH: 41 base pairs
( B ) TYPE: nucleic acid
( C ) STRANDEDNESS: single
( D ) TOPOLOGY: circular ( i i ) MOLECULE TYPE: DNA (genomic)

( x i ) SEQUENCE DESCRIPTION: SEQ ID NO:34:

TCTCTTCGAC TCTCTCTNNN NNNNNNNNNN NNNNNNNTCT C        41

( 2 ) INFORMATION FOR SEQ ID NO:35:

( i ) SEQUENCE CHARACTERISTICS:
( A ) LENGTH: 34 base pairs
( B ) TYPE: nucleic acid
( C ) STRANDEDNESS: single
( D ) TOPOLOGY: circular ( i i ) MOLECULE TYPE: DNA (genomic)

( x i ) SEQUENCE DESCRIPTION: SEQ ID NO:35:

TCTTTTCCCC ACCTTTTCTT TCTTCCTCCT TCTT        34

( 2 ) INFORMATION FOR SEQ ID NO:36:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:36:

AAGAAAGAAA AG        12

( 2 ) INFORMATION FOR SEQ ID NO:37:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:37:

TTTCTTCCTC CTTCTTTCTT TTCCCCACCT TTTC        34

( 2 ) INFORMATION FOR SEQ ID NO:38:

( i ) SEQUENCE CHARACTERISTICS:
( A ) LENGTH: 34 base pairs
( B ) TYPE: nucleic acid
( C ) STRANDEDNESS: single
( D ) TOPOLOGY: circular ( i i ) MOLECULE TYPE: DNA (genomic)

( x i ) SEQUENCE DESCRIPTION: SEQ ID NO:38:

TTTCTTTTCT CGATCTTTTC TTTCTTTTTT TTTC        34

( 2 ) INFORMATION FOR SEQ ID NO:39:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:39:

CCCTATAGTG AGTCGTATTA                                              20

( 2 ) INFORMATION FOR SEQ ID NO:40:

( i ) SEQUENCE CHARACTERISTICS:
      ( A ) LENGTH: 53 base pairs
      ( B ) TYPE: nucleic acid
      ( C ) STRANDEDNESS: single
      ( D ) TOPOLOGY: circular ( i i ) MOLECULE TYPE: DNA (genomic)

( x i ) SEQUENCE DESCRIPTION: SEQ ID NO:40:

TTTCTTCCCC CGAAGAAAAG AGAAGGAGAG AGATCCCTAG AGAGAGGAAG ACT          53

( 2 ) INFORMATION FOR SEQ ID NO:41:

( i ) SEQUENCE CHARACTERISTICS:
      ( A ) LENGTH: 53 base pairs
      ( B ) TYPE: nucleic acid
      ( C ) STRANDEDNESS: single
      ( D ) TOPOLOGY: linear ( i i ) MOLECULE TYPE: RNA (genomic)

( x i ) SEQUENCE DESCRIPTION: SEQ ID NO:41:

GGGAAGAAAA GUCUUCCUCU CUCUAGGGAU CUCUCUCCUU CUCUUUUCUU CGG          53

( 2 ) INFORMATION FOR SEQ ID NO:42:

( i ) SEQUENCE CHARACTERISTICS:
      ( A ) LENGTH: 53 base pairs
      ( B ) TYPE: nucleic acid
      ( C ) STRANDEDNESS: single
      ( D ) TOPOLOGY: circular ( i i ) MOLECULE TYPE: DNA (genomic)

( x i ) SEQUENCE DESCRIPTION: SEQ ID NO:42:

TTTCTTCCCC CGAAGAAAAG AATAAGGAAG AAGCCTCCGA AGAAGGAACA ACT          53

( 2 ) INFORMATION FOR SEQ ID NO:43:

( i ) SEQUENCE CHARACTERISTICS:
      ( A ) LENGTH: 53 base pairs
      ( B ) TYPE: nucleic acid
      ( C ) STRANDEDNESS: single
      ( D ) TOPOLOGY: linear ( i i ) MOLECULE TYPE: RNA (genomic)

( x i ) SEQUENCE DESCRIPTION: SEQ ID NO:43:

GGGAAGAAAA GUUGUUCCUU CUUCGGAGGC UUCUUCCUUA UUCUUUUCUU CGG          53

( 2 ) INFORMATION FOR SEQ ID NO:44:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: circular ( i i ) MOLECULE TYPE: DNA (genomic)

( x i ) SEQUENCE DESCRIPTION: SEQ ID NO:44:

TTATTTAGAC TTAAATAAGT TCCTCAACAT CCTTCGATGG AGCCC                   45

( 2 ) INFORMATION FOR SEQ ID NO:45:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:45:

UCUAAAUAAG GGCUCCAUCG AAGGAUGUUG AGGAACUUAU UUAAG     45

( 2 ) INFORMATION FOR SEQ ID NO:46:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: circular ( i i ) MOLECULE TYPE: DNA (genomic)

( x i ) SEQUENCE DESCRIPTION: SEQ ID NO:46:

TTTTGAACTA GAGTTTTCGG CTTTCGCCTC TTCAGAAAAG CCCTCTCTC     49

( 2 ) INFORMATION FOR SEQ ID NO:47:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:47:

GAGGGCUUUU CUGAAGAGGC GAAAGCCGAA AACUCUAGUU CAAAAGAGA     49

( 2 ) INFORMATION FOR SEQ ID NO:48:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:48:

AAAAGAGAGA GGGCUUUUCU GAAGAGGCGA AAGCCGAAAA CUCUAGUUC     49

( 2 ) INFORMATION FOR SEQ ID NO:49:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:49:

AGAGUUCAAA AGCCC     15

( 2 ) INFORMATION FOR SEQ ID NO:50:

( i ) SEQUENCE CHARACTERISTICS:

-continued

```
( A ) LENGTH: 49 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:50:

AAAAGAGAGA  GGGCUUUUCU  GAAGAGGCGA  AAGCCGAAAA  CUCUAGUUC                49
```

ROLLING CIRCLE SYNTHESIS OF OLIGONUCLEOTIDES AND AMPLIFICATION OF SELECT RANDOMIZED CIRCULAR OLIGONUCLEOTIDES

This is a continuation-in-part application of U.S. patent application Ser. No. 08/047,860, filed Apr. 15, 1993, now abandoned which is incorporated herein by reference.

STATEMENT OF GOVERNMENT RIGHTS

The present invention was made with Government support under Grant No. RO1-GM46625 awarded by the National Institutes of Health. The Government has certain rights in the invention.

FIELD OF THE INVENTION

The present invention provides methods for synthesis, selection, and amplification of DNA and RNA oligonucleotides and analogs. More specifically, the methods are directed to efficient, low-cost, and large-scale synthesis of linear and circular oligonucleotides, as well as competitive amplification and selection of DNA and RNA circular oligonucleotides having specifically selected properties.

BACKGROUND OF THE INVENTION

In recent years the availability of automated DNA synthesizers has revolutionized the fields of molecular biology and biochemistry. As a result, linear DNA oligonucleotides of specific sequences are available commercially from several companies. These can be used for a variety of applications. For example, DNA oligonucleotides can be used as primers for cDNA synthesis, as primers for the polymerase chain reaction (PCR), as templates for RNA transcription, as linkers for plasmid construction, and as hybridization probes for research and diagnostics.

DNA and RNA oligonucleotides, i.e., oligomers, also can act as sequence-specific inhibitors of gene expression through binding of a complementary, or "antisense," base sequence. See, for example, E. Uhlmann et al., *Chem. Rev.*, 90, 543 (1990), and *Oligodeoxynucleotides: Antisense Inhibitors of Gene Expression*; J. S. Cohen, Ed.; CRC Press: Boca Raton, Fla., 1989. These antisense oligomers have been shown to bind to messenger RNA at specific sites and inhibit the translation of the RNA into protein, splicing of mRNA or reverse transcription of viral RNA and other processing of mRNA or viral RNA. In addition, "anti-gene" oligomers have been developed that bind to duplex DNA and inhibit transcription.

Strong inhibitory activity has been demonstrated in vitro and in vive using these antisense and anti-gene oligomers against viruses such as HIV-1, Herpes Simplex Virus, and influenza virus, among others, as well as against several types of cancer. Thus, antisense and anti-gene oligonucleotides could be used as antiviral and anticancer agents and therapeutic agents against almost any disease mediated by gene expression. In addition, in some cases improved activity has been reported for analogs of DNA, including DNA and RNA phosphorothioates and 2'-O-methylribonucleotides. All potential therapeutic applications, however, would require large amounts (tens or hundreds of grams) of specific oligomers for animal and clinical trials, and even more for eventual use as a pharmaceutical. See, for example, I. Kitajima et al., *Science*, 258, 1792 (1992), and M. Z. Ratajczak et al., *PNAS*, 89, 11823 (1992).

One major drawback in the use of oligonucleotides as diagnostic tools or therapeutic agents is the high cost of DNA synthesis by machine using the standard solid-phase synthetic methods. Reasons for this include the high costs of the synthetically modified monomers, e.g., phosphoramidite monomers, and the fact that up to a tenfold excess of monomer is used at each step of the synthesis, with the excess being discarded. Costs of DNA oligonucleotides have been estimated at $2–5 per base for one micromole (about 3 mg of a 10 mer) on the wholesale level. On this basis, 1 gram of a 20-base oligomer would cost on the order of $20,000. Thus, significant in vivo testing of antisense oligomers will be quite expensive until ways are found to lower the cost.

Enzymatic methods have the potential for lowering the cost of oligonucleotide synthesis. Enzymatic methods use DNA or RNA nucleotide triphosphates (dNTP's or NTP's) derived from natural sources as the building blocks. These are readily available, and are less expensive to produce than phosphoramidite monomers. Generally, this is because the synthesis of the nucleotide triphosphates from base monophosphates requires as little as one step. See, for example, E. S. Simon et al., *J. Org. Chem.*, 55, 1834 (1990). In addition, the polymerase enzymes used in these methods are efficient catalysts, and are also readily available.

There are two major methods now in use for enzymatic amplification of DNA: cloning and the polymerase chain reaction (PCR). See, for example, J. Sambrook et al., *Molecular Cloning*; 2nd ed.; Cold Spring Harbor Press, 1989, and R. K. Saiki et al., *Science*, 239, 487 (1988). Cloning requires the insertion of a double-stranded version of the desired sequence into a plasmid followed by transformation of a bacterium, growth, plasmid re-isolation, and cutting out of the desired DNA by restriction endonucleases. This method is not feasible for large-scale preparation because most of the material produced (the vector) is in the form of unusable DNA sequences. PCR is a newer technique that uses a thermostable polymerase to copy duplex sequences using primers complementary to the DNA. Subsequent heating and cooling cycles allow efficient amplification of the original sequence. For short oligomers, such as those used in anti-sense applications (e.g., less than about 50 nucleotides), PCR is inefficient and not cost-effective because it requires a primer for every new strand being synthesized.

Recently, a method was developed for the enzymatic synthesis of DNA oligomers using a noncleavable linear hairpin-shaped template/primer in a PCR-like enzymatic synthesis. See G. T. Walker et al., *P.N.A.S.*, 89, 392 (1992). Although this method may be more cost-effective than PCR, the polymerase must still dissociate from the template to enable amplification. Furthermore, the end groups of the DNA produced are ragged and not well defined.

Other methods of DNA replication are discussed in Harshey et al., *PNAS USA*, 78, 1090 (1985); and Watson, *Molecular Biology of the Gene* (3rd Edition). Harshey et al., discuss the theoretical method of "roll-in" replication of double-stranded, large circular DNA. The "roll-in" process involves small, double-stranded circle cleavage and incorporation into a genome. It is primarily a process for inserting double-stranded plasmids into a double-stranded genome. Although one could conceivably use an entire genome to replicate an oligonucleotide, the resulting product would be thousands of nucleotides longer than desired. Thus, the "roll-in" process would be a very inefficient means to produce target oligonucleotide sequences. Watson briefly mentions the replication of single-stranded circles, but the author focuses the reference on the replication of double-stranded circles.

Prior to the present invention, it was thought by those skilled in the art that processive rolling-circle synthesis would not proceed without additional proteins which unwind the duplex ahead of the polymerase. See, e.g. Eisenberg et al., *PNAS USA*, 73:3151 (1976); *The Single-Stranded DNA Phages*, D. T. Denhardt et al., eds., Cold Spring Harbor Press; Cold Spring Harbor (1978); and DNA Replication, W. H. Freeman, San Francisco, 1980. In Eisenberg et al., the in vitro replication of φX174 DNA using purified proteins is disclosed. Among the listed necessary proteins are DNA unwinding protein (also known as SSB, single-strand binding protein), cisA protein, and rep protein. This DNA unwinding protein (which requires ATP) is necessary for this replicative synthesis; otherwise the polymerase stalls. *The Single-Stranded DNA Phages* includes a discussion of the mechanism of replication of a single-stranded phage and furthermore shows a scheme for this replication in FIG. 8. One of the beginning stages of replication involves the elongation of a single-stranded (−) template annealed to a full-length linear (+) strand. Any further elongation necessarily requires unwinding of the helix ahead of the polymerase. DBP (Double-strand binding protein) was thought to be necessary to coat the displaced strand in order for there to be successful DNA synthesis during elongation.

The polymerase from phage φ29 is known to amplify DNA strands as large as 70 kb in length. Even though this polymerase exhibits such a high degree of processivity, the use of the polymerase from phage φ29 still results in the wasteful (in both time and monetary resources) production of unwanted nucleotides. In order to replicate an oligonucleotide prior to the present invention, those of skill in the art would have encoded the oligonucleotide as only a small portion of the entire replicated region. Moreover, utilizing a plasmid or phage method to replicate an oligonucleotide would require the investigator to first separate the strands and then purify the oligonucleotide from thousands of other base pairs.

RNA oligomers are currently synthesized by two principal methods: DNA synthesizer and enzymatic runoff transcription. Methods have been recently published for the use of a synthesizer to construct RNA oligomers using a modification of the phosphoramidite approach. See, for example, S. A. Scaringe et al., *Nucleic Acids Res.*, 18, 5433 (1990). Because of the need for additional protecting groups, however, RNA phosphoramidite monomers are considerably more expensive than are the DNA phosphoramidite monomers, making RNA synthesis by this method extremely costly. An alternative, the enzymatic runoff transcription method, utilizes a single or double-stranded DNA template and requires a phage polymerase promoter. See, for example, J. F. Milligan et al., *Nucleic Acids Res.*, 15, 8783 (1987). In this method the RNA copy begins to form on the template after the phage polymerase promoter and runs until the end of the template is reached. This method has the disadvantages of producing RNA oligomers with ragged, ill-defined end groups and giving relatively slow amplification.

Thus, there is a need for a low-cost, fast, and efficient method for the production of DNA and RNA oligomers having well-defined ends on a large scale. In addition, there is a need to produce DNA and RNA analogs, such as, for example, DNA phosphorothioates, RNA phosphorothioates, and 2'-O-methyl ribonucleotides, with well-defined ends on a large scale and in an efficient manner. Furthermore, there is a need for a method that uses readily available enzymes and a readily prepared template to generate large amounts of a complementary sequence.

In addition, there is a need for new amplification techniques for randomized circular oligonucleotides. Recently, there has been rapid development in the generation and screening of large mixtures of nucleic acids, peptides, and related structures. These methods allow for the testing of randomized mixtures of nucleic acid sequences simultaneously as potential protein binders, inhibitors, catalysts, and the like with subsequent identification of the sequences that are the most effective protein binders, inhibitors, catalysts, and the like. Sequences that function as binders/inhibitors are useful as drugs or as lead structures in rational drug design.

The generation and screening of nucleic acids is generally more readily accomplished than that for other repeating structures. This is because nucleic acids can be amplified, which allows for more efficient selection of a smaller subset of a population. For example, if a 10-base length of nucleic acid is randomized, a mixture of up to $4^{10}$ different sequences can be obtained. The sequences can be tested for the ability to bind a protein (for example, by affinity chromatography), and a small fraction of the most successful sequences (perhaps the best 0.1%) can be separated. This still represents greater than 1000 different sequences, which to be useful, must be further selected. However, this is difficult because a very small amount of the original mixture of compounds remains. The solution is to amplify this small population to a workable amount (by PCR techniques, for example), and then to subject this mixture to further rounds of selection and amplification. As a result, a much larger population can be tested. This is in contrast to mixtures of other iteratively synthesized structures, such as peptides and peptide analogs, that cannot be amplified.

After multiple rounds of selection and amplification, linear nucleic acid sequences that are the most effective protein binders, inhibitors, catalysts, and the like can be identified. In principle, an efficient inhibitor of the protein could be directly used as a drug. Alternatively, the selected sequence may be considered a "drug lead," i.e., its structure can be analyzed and used as a model to synthesize drugs. Sequences amplified by PCR are linear and there is a need for a different structure and a different amplification technique. That is, there is a need for a more efficient method for the amplification of circular sequences that bind specific proteins, nucleic acids, and other molecules, and which may be directly used as drugs.

SUMMARY OF THE INVENTION

The present invention provides methods for the synthesis, selection, and amplification of oligonucleotides and a composition of matter comprising circular nucleic acid sequences. The methods are directed to efficient, low-cost, and large-scale synthesis of DNA and RNA oligomers and their analogs for use, for example, as probes and diagnostic and/or therapeutic agents. The selection and amplification method is advantageous because it will provide for the discovery of potential therapeutic agents. The invention also provides a composition comprising circular DNA or RNA sequences, or analogs thereof, having a randomized and a nonrandomized domain. The circular DNA sequences, RNA sequences, and analogs thereof, are selected for their ability to affect a target molecule such as a protein.

A method of the present invention for synthesizing an oligonucleotide involves the steps of providing an effective amount of an isolated circular oligonucleotide template; providing an effective amount of an isolated oligonucleotide primer; annealing the primer to the circular template to form a primed circular template; combining the primed circular template with an effective amount of at least two types of nucleotide triphosphate and an effective amount of a polymerase enzyme to form a nucleotide multimer containing multiple copies of an oligonucleotide complementary to the circular oligonucleotide template; and preferably cleaving the nucleotide multimer to produce the oligonucleotide. This method can be used to synthesize either single-stranded or double-stranded RNA and DNA linear oligonucleotides, i.e., oligomers, and their analogs, having well-defined ends upon cleavage. After formation of the linear oligonucleotides, the oligonucleotide can be circularized to form circular oligonucleotide products. The oligomers formed by the method of the present invention are capable of full sequencing and identification such that the ends are readily identifiable.

The isolated circular template is complementary to the nucleotide sequence of the desired oligonucleotide product. The isolated circular template can contain one or more copies of the complementary sequence. Preferably, a circular template has about 15–1500 nucleotides, and more preferably about 24–500 nucleotides and most preferably about 30–150 nucleotides. The desired nucleotide product sequence can be a sense, an antisense or any other nucleotide sequence including a random sequence. The oligonucleotide circular template itself may be constructed of DNA or RNA or analogs thereof. Preferably, the circular template is constructed of DNA. The oligonucleotide primer binds to a portion of the circular template and is preferably single-stranded having about 4–50 nucleotides, and more preferably about 6–12 nucleotides.

The polymerase enzyme can be any that effects the synthesis of the multimer. For the synthesis of DNA oligomers the polymerase enzyme is preferably selected from the group consisting of DNA Polymerase I, Klenow fragment of DNA Polymerase I, T4 DNA Polymerase, T7 DNA Polymerase, Taq Polymerase, AMV Reverse Transcriptase. More preferably, the polymerase enzyme is a Klenow fragment of DNA Polymerase I. For the synthesis of RNA oligomers the polymerase enzyme is preferably selected from the group consisting of T7 RNA Polymerase, T4 RNA Polymerase, SP6 RNA Polymerase, RNA Polymerase II, RNA Polymerase III, T3 RNA Polymerase and $E.\ coli$ RNA Polymerase. Closely homologous mutants of the enzymes above, i.e., mutants with greater than about 80% homology, can also be included. Further, the polymerase enzyme can be a eukaryotic RNA Polymerase.

As used herein, "an effective amount" refers to an amount of the component effective to produce multimers longer than the circular template, preferably about 4–4000 times the length of the circular template. Preferably, the primer is provided in an amount of about 0.1–100 moles per mole of circular template, and the nucleotide triphosphates are provided in an amount of about 50–$10^7$ and more preferably 200–$2\times10^6$ moles per mole of circular template. As used herein, "oligonucleotide" and "oligomer" are used interchangeably to refer to a sequence-defined and length-defined nucleic acid or analog thereof, whereas a "multimer" is a repeated nucleic acid linear polymer containing end to end copies of an oligomer.

The present invention is also directed to a method of amplifying and selecting circular oligonucleotides having a random domain. A population of circular DNA or RNA sequences, or analogs thereof, having randomized sequences are selected for the capacity to affect a target molecule. Preferably, a selection method includes binding of the circular molecule to a target protein, RNA, or DNA sequences. Other selection methods include inhibition of a functional activity of a protein such as enzyme activity, ability to catalyze a reaction, gel-shift assays, and precipitation methods. Preferably, the initial screening of the population of DNA or RNA sequences, or analogs thereof, is conducted by detecting those sequences that bind to the target molecule using affinity chromatography. The selected circular sequences are then amplified, preferably, with the rolling circle method of amplification described herein. Preferably, the selected circular sequences are amplified and selected to generate a selected population of circular sequences. The selected population of circular sequences is homogenous in the capacity to bind to and/or otherwise affect the function of the target molecule. The circular nucleic acid sequences in the selected population can be identified and isolated by standard methods. From this selected population of circular sequences having comparable functional activity individual circular sequences can be identified and amplified. Each individual circular sequence, whether DNA, RNA or analogs thereof can be useful as a pharmaceutical compound or as a "drug lead" in the synthesis of pharmaceutical compounds.

The present invention is also directed to circular oligonucleotides having a randomized domain and a constant domain. Preferably, a population of circular oligonucleotides is composed of isolated circular nucleic acid sequences that can modify the structure or function of a target molecule. The circular nucleic acid sequence includes a randomized domain linked to a constant domain having a different sequence, wherein the constant domain comprises a primer binding sequence and a cleavage sequence.

The present invention includes single-stranded circular polynucleotide templates. These circular polynucleotide templates have a binding domain that is complementary to a sequence that can bind to the target molecule, a constant domain having a primer binding sequence, and a structural domain complementary to a structural sequence. The binding domain is that portion of the circular nucleic acid molecule that encodes a binding sequence that can bind to target nucleic acids or target proteins. The structural domain encodes a structural sequence that is a stem-loop sequence, a hairpin sequence, a hammerhead-type ribozyme or a hairpin-type ribozyme. The target molecule of the circular oligonucleotide can be HIV-1 gag, HIV reverse transcriptase, HIV tat protein, squalene synthase, FK506 binding protein, mutated p53 protein, mutated K-ras protein, bcr-abl mutant protein, restriction endonucleases, influenza coat protein, opiate receptors, transcription repressor proteins, multidrug resistance protein, d-ala-d-ala, d-ala-d-lactate, rhinovirus coat proteins, bcl-2 protein, thrombin, and nitric oxide synthase. The present invention also includes methods for modifying the function of a target molecule in a cell where a single-stranded circular oligonucleotide containing a random domain, a constant domain having a primer binding site and a cleavage site, and a structural domain is introduced into cells. The structural domain can be a stem-loop sequence, a hairpin sequence, a hammerhead-type ribozyme or a hairpin-type ribozyme.

DETAILED DESCRIPTION OF THE INVENTION

Figure 1:
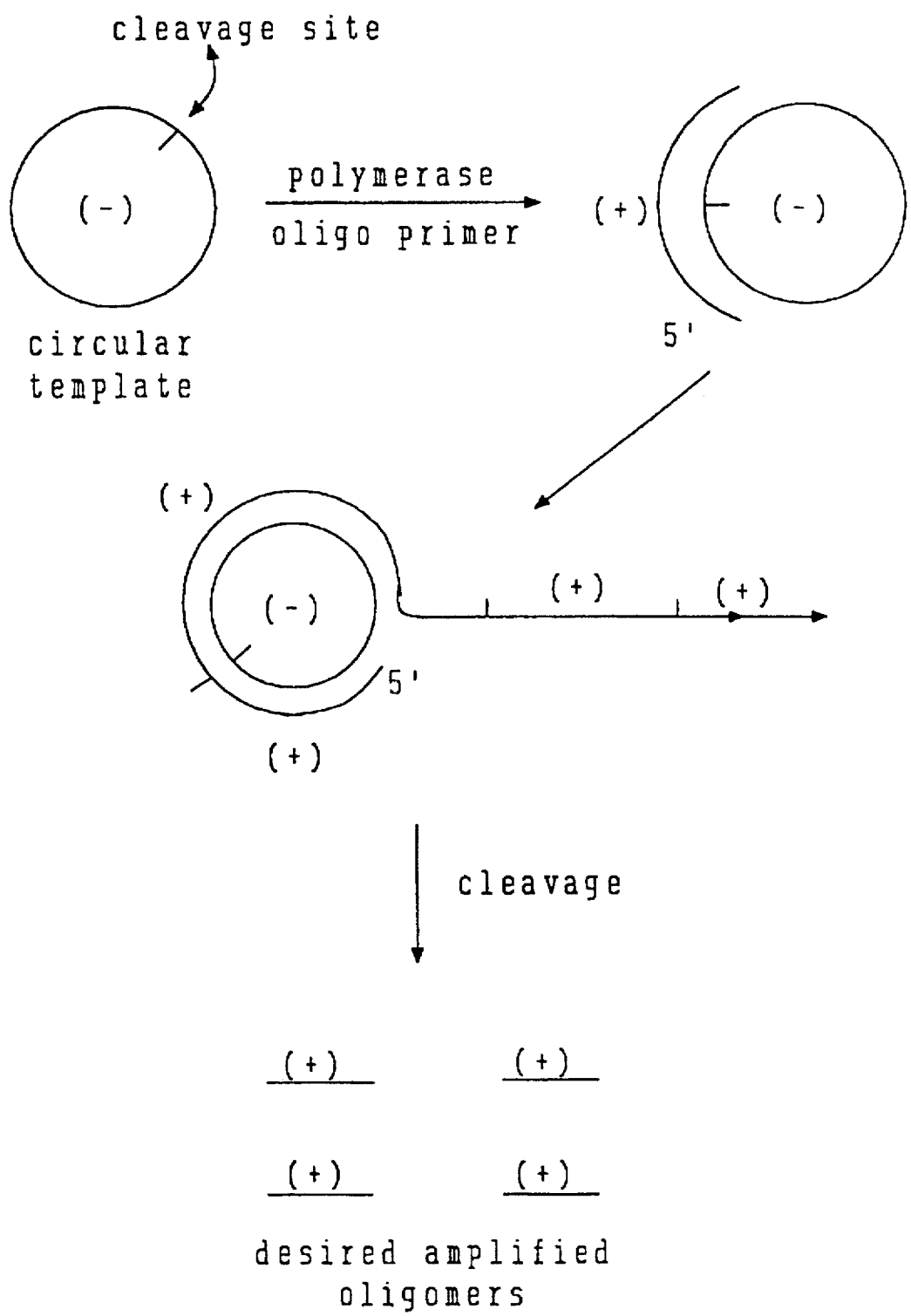
FIG. 1. Schematic of the rolling circle synthetic method of the present invention.

The present invention provides methods for synthesis, selection, and amplification of oligonucleotides, i.e., oligomers. The synthetic method, which can also be used as the amplification method, is directed to efficient, low-cost, and large-scale production of DNA and RNA oligomers and analogs thereof, for use as probes, diagnostic agents, and therapeutic agents. A method is also provided that provides for the selection and amplification of circular DNA or RNA sequences as a result of specific properties, such as their ability to bind a specific protein, nucleic acid, or other molecule. This selection method will thus aid in the discovery of new and better types of therapeutically active drug leads and therapeutic oligonucleotides, particularly circular oligonucleotides. The circular oligonucleotides of the invention have a randomized domain and a constant domain and are selected for the capacity to affect a target molecule.

As used herein, "oligonucleotides" or "oligomers" refer to a sequence and length defined nucleic acid sequence or analog thereof as the desired product of the method of synthesis of the invention. A "multimer" is a nucleic acid sequence containing multiple copies of the oligomer joined end to end. An "isolated circular template" refers to a circular nucleic acid sequence including a sequence complementary to the desired oligomer that is formed by circularization of a linear precircle. An "isolated oligonucleotide primer" refers to a nucleic acid sequence that is sufficiently complementary to a nucleic acid sequence of the circular template to bind to the isolated circular template and acts as a site for initiation of synthesis of a multimer. A "sense" sequence refers to a DNA sequence that encodes the information for a protein product. An "antisense" sequence refers to a DNA sequence complementary to a sense sequence that can bind to a sense sequence and inhibit its expression. A "randomized domain" refers to a DNA or RNA sequence, or analog thereof, containing nucleic acids in a random sequence. An "effective" amount refers to an amount of a component effective to produce multimers longer than the circular template. A "drug lead" refers to a molecule that affects the function or structure of a target biomolecule and is used to design other pharmaceutical compounds having similar molecular shape or composition and function.

Specifically, the present invention provides a novel, inexpensive, and simple method for the enzymatic construction of DNA and RNA oligonucleotides, or analogs thereof, having a specific sequence and well-defined ends. This synthetic method has several advantages over presently used techniques. First, the cost of oligomers produced by this method is lower than that of machine-synthesized or PCR-generated oligomers. Previous methods of amplifying a target nucleic acid sequence using circular replication methods used plasmid-sized DNA of several thousand nucleotides long. These previous amplification methods therefore produced sequences thousands of nucleotides in length even when the sequence of interest may only have been a few dozen nucleotides long. Thus, the amplification reactions would consume a large quantity of nucleotides while only a comparatively small amount of the nucleotides actually were components in the desired product.

Second, the method of the present invention is very simple and produces relatively pure oligomers. Because the method of the present invention does not incorporate unwanted nucleotides into the product molecules, the resulting oligonucleotides are easier to purify than those oligomers resulting from the prior art methods of replication. Third, the method does not consume costly organic solvents or other reagents. Nor does it generate costly organic waste.

The method of the present invention can be applied to the synthesis of oligomers having about 4 to about 1500 bases in length. Herein, the synthetic method is referred to as the rolling circle method. This method involves the synthesis of single-stranded multimers complementary to a circular template.

The rolling circle synthetic method of the present invention advantageously uses readily available enzymes and a chemically prepared template to generate large amounts of a complementary oligonucleotide sequence. The method is advantageous because it uses only a small excess of nucleotide triphosphates, with the unused portions being recycled, and a catalytic amount of primer. Furthermore, it produces oligomers with well-defined ends. Also, the direct product of the reaction is reasonably pure, and can be further purified very easily using standard techniques, if desired.

This synthetic method is ideal for the large-scale preparation of desirable oligomers of DNA or RNA, such as the commercially sold hybridization primers, PCR primers, or specific randomized circular nucleotides that have been (or will be) shown to be of potential therapeutic value. It is a very efficient method that does not require bacterial culture or thermal cycles, and requires only catalytic, not stoichiometric, amounts of a primer. Finally, the method is also an efficient approach to producing circular oligonucleotides.

The present invention also provides a novel method for the amplification and selection of novel circular nucleic acid sequences with certain advantageous properties. For example, circular oligonucleotides effective for binding a specific protein, nucleic acid, or other target molecule or receptor can be selected. The method involves synthesis of a population of circles containing a randomized domain, followed by selection of the most successful sequences in the mixture. Successful sequences are ones that have the highest binding affinity or have the best ability to affect a function of the target molecule. Selection methods include affinity chromatography, immunoprecipitation, equilibrium dialysis, gel shift analysis, blot or paper hybridization, and coprecipitation. These methods separate circular nucleic acid sequences that are more tightly bound from those that are more weakly bound. Circular sequences that are more tightly bound to the target molecule are preferably selected and then amplified.

The set of selected circular oligonucleotides is then amplified by the rolling circle method, i.e., the synthetic method of the present invention, optionally with further rounds of selection as described above. This allows screening of a large initial population of molecules and identification of successful select circular sequences. The successful selected circular sequences form a population of circular DNA sequences that are homogeneous in their function to bind to and/or affect a target molecule. From this population of selected circular DNA sequences, individual sequences can be identified and amplified. Any one of the individual circular DNA so identified and amplified from the selected population can be used as a pharmaceutical compound or as a "drug lead". Such selected circles could be useful in a variety of applications, such as in the identification of binders/inhibitors of a specific protein or nucleic acid, and as nuclease-resistant drugs.

Circular oligomers have distinct advantages over linear oligomers. First, since the circular structure is more rigid, it will result in compounds that bind more strongly to the desired target. In addition, this greater rigidity allows easier identification of the shape of the bound species, thus making a better drug lead. Furthermore, the best circular oligomers may be potential drugs themselves, at least because they are highly stable. Circular DNA oligomers have a half-life of greater than about two days in human serum (as compared to a half-life of about twenty minutes for linear oligomers). See, for example, S. Rumney and E. Kool, *Angew. Chem., Intl. Ed. English*, 31, 1617 (1992). The combination of this stability with the greater binding affinity makes this approach advantageous.

Rolling Circle Synthesis of Oligomers

The method of the invention for the synthesis of DNA and RNA oligomers, and synthetically modified analogs thereof, such as, for example, DNA phosphorothioates, RNA phosphorothioates, 2'-O-methyl ribonucleotides, involves these general steps: (1) providing an effective amount of an isolated single-stranded oligonucleotide circular template and an effective amount of an isolated single-stranded oligonucleotide primer; (2) annealing the oligonucleotide primer to the oligonucleotide circular template to form a primed circular template; (3) combining the primed circular template with an effective amount of at least two types of nucleotide triphosphates and an effective amount of a polymerase enzyme to form a single-stranded nucleotide multimer complementary to the circular oligonucleotide template; and preferably (4) cleaving of the single-stranded nucleotide multimer into the desired single-stranded oligonucleotides, i.e., oligomers, and optionally circularizing an oligonucleotide to form a circular product of DNA, RNA, or analog thereof.

In a standard reaction, this method requires only very small amounts of the circular template, primer, and polymerase enzyme, i.e., only an effective catalytic amount for each component. Surprisingly, no auxiliary proteins need to be added to assist the polymerase. A relatively larger amount, i.e., a stoichiometric amount, of the nucleotide triphosphates is required. After the reaction, the mixture consists of a large amount of the product oligomer and only small amounts of the template, primer, polymerase enzyme, and cleaving enzyme or reagent. Thus, the product is produced in relatively good purity, and can require only gel filtration or dialysis before use, depending on the application. Advantageously, the polymerase enzyme, the circular template, unreacted primer, and unreacted nucleotide triphosphates can be recovered for further use.

The rolling circle method of the present invention is also advantageous for many reasons including the following: (1) it allows optimum production of single-stranded oligonucleotides, unlike PCR and cloning; (2) it uses lower amounts of nucleotide units in the synthesis as compared to DNA synthesizers; (3) it requires only a catalytic amount of circular template and primer (PCR requires stoichiometric amounts of primer); (4) it produces oligomers having clean, well-defined ends (unlike runoff transcription); (5) it is more efficient than single-stranded PCR amplification or runoff transcription because the polymerase enzyme is not required to associate and dissociate from the template in cycles; (6) expensive thermal cyclers and thermostable polymerases are not required; (7) it is possible to make DNA and RNA oligomers and analogs by this method using the same templates; (8) it is better suited for synthesis of circular oligonucleotides; (9) it allows for production in very large batches (hundreds or thousands of grams); (10) it does not use organic solvents or potentially toxic reagents; (11) fewer errors in the sequences are made (machine-synthesized DNA contains structural errors about every 50–100 bases or so, whereas enzyme methods make errors at the rate of about 1 in $10^4$–$10^8$ bases); and (12) the product generally needs relatively little purification (perhaps gel filtration or dialysis) because only small amounts of template and polymerase are needed to produce large amounts of oligomer. Thus, the present invention reduces, and in certain situations completely eliminates, difficult and expensive large-scale chromatographic purification.

Construction of circular template. In order to conduct the synthetic method of the invention, an isolated circular oligonucleotide template is provided. For a desired oligomer, a circular oligonucleotide template which is complementary in sequence to the desired oligonucleotide product can be prepared from a linear precursor, i.e., a linear precircle. The template linear precircle has a 3'- or 5'-phosphate group. If the desired oligonucleotide product sequence is short (i.e., less than about 20–30 bases), a double or higher multiple copy of the complementary sequence can be contained in the template circle. This is generally because enzymes cannot process circular sequences of too small a size. Typically, a circular template has about 15–1500 nucleotides, preferably about 24–500, and more preferably about 30–150 nucleotides. It is to be understood that the desired nucleotide product sequence can either be a sense, antisense, or any other nucleotide sequence.

The circular oligonucleotide template also has encoded within it a group that will be cleavable in the transcript, i.e., the nucleotide multimer product. That is, for restriction enzyme cleavage, it will contain a restriction sequence. For example, the sequence 5-...G A T C...-3' will be cleaved immediately before the G by the enzyme Sau3AI. The product oligomers will contain the sequence on the 5' end. If a restriction sequence in the resultant oligomer is not desirable, a Type-II restriction site can be encoded within a hairpin forming sequence, so that the entire cleavable group will be removed by the cleaving enzyme, leaving only the desired sequence, as in Example 3. Another method, described by Szybalski et al., *Gene*, 40, 169 (1985), uses an added oligomer to direct a Type-II restriction enzyme to cleave at any desired sequence. Finally, a specific cleavable group might also be a natural DNA base, which could be cleaved chemically, as in Examples 2 and 8, or it could be a modified base, as in Example 9 or 10.

Linear precircle oligonucleotides, from which the circular template oligonucleotides are prepared, can be made by any of a variety of procedures known for making DNA and RNA oligonucleotides. For example, the linear precircle can be synthesized by any of a variety of known techniques, such as enzymatic or chemical, including automated synthetic methods. Furthermore, the linear oligomers used as the template linear precircle can be synthesized by the rolling circle method of the present invention. Many linear oligonucleotides are available commercially, and can be phosphorylated on either end by any of a variety of techniques.

Linear precircle oligonucleotides can also be restriction endonuclease fragments derived from naturally occurring DNA sequence. Briefly, DNA isolated from an organism can be digested with one or more restriction enzymes. The desired oligonucleotide sequence can be isolated and identified by standard methods as described in Sambrook et al., *A Laboratory Guide to Molecular Cloning*, Cold Spring Harbor, N.Y. (1989). The desired oligonucleotide sequence can contain a cleavable site, or a cleavable site can be added to the sequence by ligation to a synthetic linker sequence by standard methods.

Linear precircle oligonucleotides can be purified by polyacrylamide gel electrophoresis, or by any number of chromatographic methods, including gel filtration chromatography and high performance liquid chromatography. To confirm a nucleotide sequence, oligonucleotides can be subjected to RNA or DNA sequencing by any of the known procedures. This includes Maxam-Gilbert sequencing, Sanger sequencing, capillary electrophoresis sequencing automated sequencing, wandering spot sequencing procedure, or by using selective chemical degradation of oligonucleotides bound to Hybond paper. Sequences of short oligonucleotides can also be analyzed by plasma desorption mass spectroscopy or by fast atom bombardment.

The present invention also provides several methods wherein the linear precircles are then ligated chemically or enzymatically into circular form. This can be done using any standard techniques that result in the joining of two ends of the precircle. Such methods include, for example, chemical methods employing known coupling agents such as BrCN plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. Furthermore, the ends of a precircle can be joined by condensing a 5'-phosphate and a 3'-hydroxyl, or a 5'-hydroxyl and a 3'-phosphate. Enzymatic circle closure is also possible using DNA ligase or RNA ligase under conditions appropriate for these enzymes.

One enzymatic approach utilizes T4 RNA ligase, which can couple single-stranded DNA or RNA. This method is described in D. C. Tessier et al., *Anal Biochem.*, 158, 171–178 (1986), which is incorporated herein by reference. Under high dilution, the enzyme ligates the two ends of an oligomer to form the desired circle. Alternatively, a DNA ligase can be used in conjunction with an adaptor oligomer under high dilution conditions.

Preferably, the method of forming the circular oligonucleotide template involves adapter directed coupling. Methods such as this are described in the Examples and in G. Prakash et al., *J. Am. Chem. Soc.*, 114, 3523–3527 (1992), E. T. Kool, PCT Publication WO 92/17484, and E. Kanaya et al., *Biochemistry*, 25, 7423–7430 (1986), which are incorporated herein by reference. This method includes the steps of: hybridizing a linear precursor having two ends to an adapter, i.e., a positioning oligonucleotide, to form an open oligonucleotide circle; joining the two ends of the open oligonucleotides circle to form the circular oligonucleotide template; and recovering the single-stranded circular oligonucleotide template. The positioning oligonucleotide is complementary to the two opposite ends of the linear precursor. The precursor and the adapter are mixed and annealed, thereby forming a complex in which the 5' and 3' ends of the precircle are adjacent. The adapter juxtaposes the two ends. This occurs preferentially under high dilution, i.e., no greater than about 100 micromolar, by using very low concentrations of adapter and precursor oligomers, or by slow addition of the adapter to the reaction mixture. These ends then undergo a condensation reaction, wherein the 5'-phosphate is coupled to the 3'-hydroxyl group or the 3'-phosphate is coupled to the 5'-hydroxyl group, after about 6–48 hours of incubation at about 4°–37° C. This occurs in a buffered aqueous solution containing divalent metal ions and BrCN at a pH of about 7.0. Preferably, the buffer is imidazole-HCl and the divalent metal is Ni, Zn, Mn, Co, Cu, Pb, Ca, or Mg. More preferably, the metals are Ni and Zn. Other coupling reagents that work include 1-(3-dimethylaminopropyl)-3 ethylcarbodiimide HCl, and other water-soluble carbodiimides, or any water-active peptide coupling reagent or esterification reagent.

The circular oligonucleotide template can be purified by standard techniques although this may be unnecessary. For example, if desired the circular oligonucleotide template can be separated from the positioning oligonucleotide by denaturing gel electrophoresis or melting followed by gel electrophoresis, size selective chromatography, or other appropriate chromatographic or electrophoretic methods. The isolated circular oligonucleotide can be further purified by standard techniques as needed.

Construction of primer. The primer used in the rolling circle method is generally short, preferably containing about 4–50 nucleotides, and more preferably about 6–12 nucleotides. This primer is substantially complementary to part of the circular template, preferably to the beginning of the desired oligomer sequence. A substantially complementary primer has no more than about 1–3 mismatches while still maintaining sufficient binding to the template. The 3' end of the primer must be at least about 80%, preferably 100%, complementary to the circular template. There is no requirement that the 5' end be complementary, as it would not have to bind to the template. Although a portion of the primer does not have to bind to the circular template, about 4–12 nucleotides should be bound to provide for initiation of nucleic acid synthesis. The primer can be synthesized by any of the methods discussed above for the linear precircle oligomer, such as by standard solid-phase techniques. See, for example, S. L. Beaucage et al., *Tetrahedron Lett.*, 22, 1859 (1981) (for DNA), and S. A. Scaringe et al., *Nucleic Acids Res.*, 18, 5433 (1990) (for RNA).

An effective amount of the primer is added to the buffered solution of an effective amount of the circular template under conditions to anneal the primer to the template. An effective amount of the primer is present at about 0.1–100 moles primer per mole of circular template, preferably 0.1–10. An effective amount of the circular template is that amount that provides for sufficient yield of the desired oligomer product. The effective amount of the circular template depends on the scale of the reaction, the size and sequence of circular template, and the efficiency of the specific rolling circle synthesis. Typically, the amount of the circular template is present at about a 1:5 to 1:20,000 ratio with the amount of desired oligomer product, i.e., 1–5000 fold amplification, preferably 1:50 to 1:5000 ratio.

Conditions that promote annealing are known to those of skill in the art for both DNA-DNA compositions and DNA-RNA compositions and are described in Sambrook et al., cited supra. Once formed, the primed circular template is used to initiate synthesis of the desired oligomer or multimer.

Rolling circle synthesis. Rolling circle synthesis is initiated when nucleotide triphosphates and polymerase are combined with a primed circular template. At least two types of nucleotide triphosphate, along with an effective catalytic amount of the desired polymerase enzyme are added (see FIG. 1) to the mixture of the primer and circular template. Amplified run-on synthesis then occurs: the polymerase starts at the primer, elongates it, and continues around the circle, making the desired oligonucleotide product sequence. It continues past the starting point, displacing the synthesized DNA (or RNA) as it goes, and proceeds many times around the circle. This produces a long single multimer strand which is made up of many end-to-end copies of the desired oligonucleotide product. The size of the multimer product can be about 60 to $5 \times 10^6$ nucleotides in length. More preferably, the multimer product is about 500–100,000 nucleotides in length.

The length of the multimer can be controlled by time, temperature, relative and absolute concentrations of enzyme, triphosphates, template, and primer. For example, longer periods of time, or lower concentrations of template, will tend to increase the average multimer length. The rolling circle method preferably uses only catalytic amounts of template, primer, and polymerase enzymes and stoichiometric amounts of the nucleotide triphosphates. Typically, the maximum size of multimer product is unlimited, however, often it is about $10^4$–$10^6$ nucleotides in length.

More preferably, the template concentration is about 0.1 µM to about 1 mM, the primer concentration is about 0.1 µM to about 1 mM, and the triphosphate concentration is about 1 µM to about 1000 mM. The preferred molar ratio of triphosphate(s) to template is about 50:1 to about $10^7$:1. The preferred molar ratio of primer to template is about 0.1:1 to about 100:1. These preferred amounts, i.e., concentrations and molar ratios, refer to amounts of the individual components initially provided to the reaction mixture.

The preferred reaction time for the rolling circle synthesis is about 1 hour to about 3 days. Preferably, the temperature of the reaction mixture during the rolling circle synthesis is about 20°–90° C. For polymerase enzymes that are not thermally stable, such as DNA polymerase I and its Klenow fragment, and other nonengineered enzymes, the temperature of synthesis is more preferably about 20°–50° C. For thermostable polymerases, such as that from *Thermus aquaticus*, the temperature of synthesis is more preferably about 50°–100° C.

Oligomers may be radiolabeled if desired by adding one radiolabeled base triphosphate to the reaction mixture along with the unlabeled triphosphates at the beginning of the reaction. This produces multimer and product oligomers that are radiolabeled internally. For example, spiking the reaction mixture with $\alpha$-$^{32}$P-dCTP will produce oligomers internally labelled with $^{32}$P at every C residue. Alternatively, a radiolabeled primer oligomer can be used, which results in a 5' radiolabeled multimer.

Preferred polymerase enzymes that effectuate the synthesis of a multimer in rolling circle synthesis have high fidelity, high processivity, accept single-stranded templates, and have relatively low exonuclease activity. For DNA polymerization, i.e., formation of DNA multimers, suitable enzymes include, but are not limited to, DNA Polymerase I, Klenow fragment of DNA Polymerase I, T7 DNA Polymerase (exonuclease-free), T4 DNA Polymerase, Taq Polymerase, and AMV (or MuLV) Reverse Transcriptase or closely homologous mutants. This group of enzymes is also preferred. More preferably, the enzyme for DNA polymerization is the Klenow enzyme. For RNA polymerization, i.e., formation of RNA multimers, suitable enzymes include, but are not limited to, the phage polymerases and RNA Polymerase II. Preferred enzymes for RNA polymerization are T7, T4, and SP6 RNA Polymerases, as well as RNA Polymerase II and RNA Polymerase III or closely homologous mutants.

Useable nucleotide triphosphates are any that are used in standard PCR or polymerase technology. That is, any nucleotide triphosphate can be used in the rolling circle method that is capable of being polymerized by a polymerase enzyme. These can be both naturally occurring and synthetic nucleotide triphosphates. They include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP as well as the alphathiotriphosphates for all of the above, and 2'-O-methyl-ribonucleotide triphosphates for all the above bases. Preferably, the nucleotide triphosphates are selected from the group consisting of dATP, dCTP, dGTP, TTP, and mixtures thereof. Modified bases can also be used in the method of the invention including, but not limited to, 5-Br-UTP, 5-Br-dUTP, 5-F-UTP, 5-F-dUTP, 5-propynyl dCTP, and 5-propynyl-dUTP. Most of these nucleotide triphosphates are widely available from commercial sources such as Sigma Chemical Co., St. Louis, Mo. Nucleotide triphosphates are advantageously used in the method of the present invention at least because they are generally cheaper than the nucleotide precursors used in machine synthesis. This is because the nucleotide triphosphates used herein are synthesized in as little as one step from natural precursors.

The rolling circle method of the present invention can also be used to produce double-stranded DNA oligomers, if desired. This is carried out by one of two methods. Rolling circle synthesis can be carried out separately on each of the complementary strands, and the multimer products combined at the end and then cleaved to give the desired duplex oligomers. Alternatively, two complementary circular templates can be placed in the reaction mixture simultaneously along with one primer for each strand (the primers are not complementary to each other). In this way, two primed circular templates are formed. The rolling circle synthesis can be carried out for both the complementary strands at the same time. That is, amplified run-on synthesis occurs with each primed circular template. This is possible because the two circular templates, although complementary to each other in sequence, cannot hybridize completely with each other as they are topologically constrained. As the complementary multimeric strands are formed, they combine to form the desired double-stranded multimer. This double-stranded multimer can then be cleaved to produce the desired double-stranded oligomers having well-defined ends.

The products generated from the synthetic method include linear or circular, single or double stranded DNA or RNA or analog multimer. The multimer can contain from about 60 to about $5 \times 10^6$ nucleotides, preferably about 500–100,000, or about 5–100,000 copies of the desired nucleotide sequences. Once formed, a linear multimer containing multiple copies of the desired sequence can be cleaved into single copy oligomers having the desired sequence either while synthesis is occurring or after oligonucleotide synthesis is complete.

Cleavage of multimer into desired oligomers. The multimer can be cleaved into single-stranded oligomers by a variety of methods. Similarly, the double-stranded multimer can be cleaved into double-stranded oligomers. Cleavage can be carried out during the rolling circle stage, i.e., as the multimer is formed, by adding both the polymerase and a cleaving agent to the solution. Alternatively, cleavage can be carried out after the polymerase reaction, and the multimer is completely formed. Purification of the resultant oligomer can then be carried out if desired. Also, if desired, at this stage the synthesized oligomers can be cyclized into new circles for use as DNA/RNA binding agents, therapeutic or diagnostic agents, or as templates for the rolling circle synthesis of the complementary strand.

There are several techniques that can be used for the cleavage reaction. For example, restriction endonucleases can be used to cleave specific sequences that occur in the multimer. They can be used alone, or in some cases, with addition of a short DNA strand that aids in the reaction. The cleavage reaction also can be carried out using chemicals other than enzymes to effect cleavage of the multimer. For example, Maxam-Gilbert cleavage reagents can be used to cleave the strand at a base that occurs once between each oligomer.

For cleavage of RNA multimers, enzymatic or chemical techniques can be used. The enzyme RNase H can be used along with addition of a DNA oligomer, or base-specific RNases can be used. Alternatively, a catalytic ribozyme can be used to cleave the multimer, or a self-cleaving sequence can be encoded in the multimer, which would then cleave itself at the desired sites. For example, a self-cleaving multimer would result from inclusion of the hammerhead sequence (A. C. Forster et al., *Cold Spring Harbor Symp. Quant. Biol.*, 52, 249 (1987)) in the RNA oligomer. Alternatively, an RNA multimer could also be cleaved at any sequence by using a sequence-specific ribozyme, such as from the hammerhead sequence used in trans. See J. Haseloff et al., *Nature*, 334, 585 (1988). Another example of cleavage of an RNA multimer would be specific cleavage between G and A in the sequence 5'-GAAA, which can be achieved by the addition of the oligomer 5'-UUU and $Mn^{2+}$, following the method of Altman described in S. Kazakov et al., *Proc. Natl. Acad. Sci. USA*, 89, 7939–7943 (1992), which is incorporated herein by reference. RNA can also be cleaved using catalysts such as those described in J. Chin, *J. Am. Chem. Soc.*, 114, 9792 (1992), incorporated herein by reference, which have been attached to a DNA oligomer for sequence specificity.

For DNA, any one of several methods can be used as well. For example, the strand can be cut at a restriction enzyme site that has been incorporated into the sequence, leaving the restriction sequence in the oligomer product. This is demonstrated by Examples 1 and 7. Optionally, the remaining restriction site sequences can be removed from the oligonucleotide with an exonuclease or another restriction or nuclease enzyme. A hairpin sequence can be cut out using a Type II restriction enzyme. This is demonstrated by Example 3. The strand can be cut at any desired site using a Type II restriction enzyme and the method of Szybalski as described in W. Szybalski, *Gene*, 40, 169 (1985), and A. Podhadjska et al., *Gene*, 40, 175 (1985), which are incorporated herein by reference.

The Szybalski and Podhadjska et al. references concern the use of FokI restriction enzyme and an adapter oligonucleotide to cleave DNA at predetermined sites, i.e., they disclose a method of providing enzyme specificity by synthetic design. That is, these references disclose methods for cleaving of DNA, but not methods for amplifying DNA. The result of the method disclosed by these references is a double-stranded DNA molecule that contains a recognition sequence for class IIS restriction endonucleases.

If the nucleotide sequence of the desired oligomer does not contain all four bases, the fourth base can be added once per repeat and cleaved from the specifically by the Maxam-Gilbert methods, thereby producing oligomers with 3'- and 5'-phosphate end groups. This is done by encoding the complement of this fourth base, or any other cleavable nucleotide, either natural or modified, into the circular oligonucleotide template. Maxam-Gilbert methods are described in J. Sambrook et al., *Molecular Cloning*, 2nd ed.; Cold Spring Harbor Press, 1989, which is incorporated herein by reference.

Chemical cleavage of a nucleotide multimer at a natural nucleotide incorporated into the multimer is demonstrated by Examples 2, 8 and 11. Cleavage of a multimer at a modified nucleotide is demonstrated by Example 9. In this example, a base is modified with a photolabile group, such as an ortho-nitrobenzyl group, which is cleaved by light. Alternatively, an incorporated modified base can be used to cleave a multimer by specific chemical or redox signals, leaving the desired oligomers.

Another possibility for cleavage of the nucleotide multimers formed by the rolling circle synthesis of the present invention is the development of sequence-specific endonucleases. For example, S1 nuclease can be attached covalently to a linear or circular oligomer to give cleavage at specific sequences. RNase H can also be attached to such oligomers for cleavage of RNA.

Once the multimer is cleaved into the oligomer, the oligomer can be isolated by standard methods. The oligomer can also be circularized using the same methods described for circularizing a linear precircle into the circular template as described herein.

Competitive Selection/Amplification Methods

A method of the invention also includes a screening and amplification method to identify circular nucleotide sequences that bind to and/or alter the function of proteins or other biological targets. This method of the invention provides for the screening of circular nucleotide sequences with random sequences linked by a common known oligonucleotide linker to generate a population of selected sequences. The linker serves as a primer binding site for further amplification of the desired random nucleotide sequence and as a cleavage site in the multimer copy.

A population of circular nucleotide sequences having randomized domains is generated. A circular nucleotide sequence includes a randomized domain of DNA or RNA sequence and a known constant domain of DNA or RNA. The known constant or nonrandom domain provides for a binding site for an oligonucleotide primer and a cleavage site for cleaving multimers into oligomers. Preferably, the randomized domain contains about 5–1400 bases and more preferably about 5–190 bases. Preferably, the known constant domain contains about 5–100 bases and more preferably about 8–40 bases in length. The initial population of circular sequences is a mixture of circular sequences having different randomized sequences and having the same known constant domain sequence. The mixture preferably contains about $1000–10^{13}$ different circular DNA or RNA sequences and more preferably about $10,000–10^{11}$ different circular DNA or RNA sequences. The initial population of circular sequences is then selected for the capacity to affect the structure or function of a target molecule.

The target molecules of the invention are biomolecules such as proteins, DNA, or RNA sequences. The circular sequences are selected for the capacity to bind and/or functionally modify the activity of the biomolecule. Specific examples of target molecules include HIV reverse transcriptase, HIV tat protein, squalene synthase, FK506 binding protein, mutated p53 protein, mutated K-ras protein, bcr-abl mutant protein, restriction endonucleases, influenza coat protein, opiate receptors, transcription repressor proteins, multidrug resistance protein, d-ala-cl-ala, d-ala-cl-lactate, rhinovirus coat proteins, bcl-2 protein, thrombin, nitric oxide-synthase and messenger RNA's or DNA sequences that control or encode these proteins.

Figure 2:
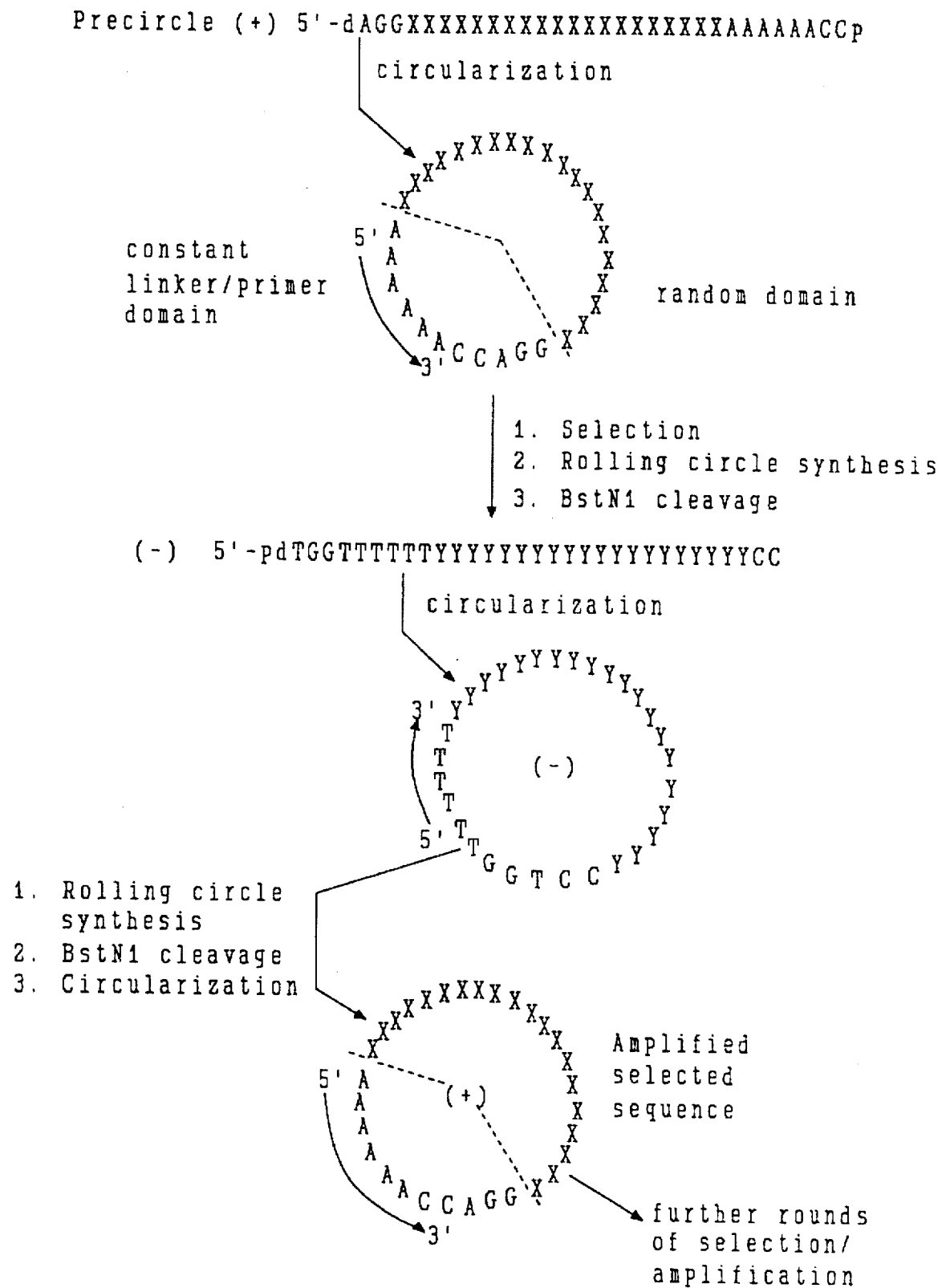
FIG. 2. Schematic of the selection and amplification of a circular oligomer (SEQ ID NO:23), (SEQ ID NO:24), (SEQ ID NO:25), AND (SEQ ID NO:26).

The selection of the circular nucleotide sequences can be accomplished by affinity chromatography or any one of several techniques with the desired protein or other target molecule. These techniques can be based on, for example, inhibition of enzyme activity, catalysis of enzyme activity, cleavage of RNA, DNA, or peptide bonds, penetration of a biological membrane, or the ability to inhibit transcription or translation of gene encoding a protein. In a preferred version, the initial selection method is by binding of the circular molecules to the target molecule. Referring to FIG. 2, a target molecule, as for example, a protein whose function is easily assayed, is chosen for the binding selection assay. It is then crosslinked to a solid support using published techniques, such as those in A. D. Ellington et al., *Nature*, 346, 818–822 (1990), which is incorporated herein by reference. This modified support (sephadex, cellulose, silica, polystyrene, etc.) is placed in a chromatography column, to be used in affinity chromatography to select for these circular nucleotide sequences that bind to the protein.

This population of desired circular sequences in aqueous solution is then contacted with the affinity column containing the solid support with the target protein (or other target molecule) attached. The sequences having little or no affinity for the target protein are eluted quickly, and the higher affinity sequences are eluted in later volumes. The higher affinity sequences are more tightly bound to the column and are eluted in later volumes or by using denaturing conditions. Elution conditions commonly used in affinity chromatography include elution at high or low pH, elution with a salt gradient or elution with a detergent such as sodium dodecyl sulfate or denaturant such as urea or guanidium salts. Techniques employed in affinity chromatography to prepare and elute molecules from affinity columns are known to those of skill in the art and as described in *Affinity Chromatography: Practical & Theoretical Aspects*; Ed: P. Mohr; Dekker Publishing; New York (1985). While not in any way meant to limit the invention, the affinity of the preferred selected circular sequences should be comparable to the binding of a natural substrate for the enzyme or antigen for the antibody or transcriptional regulatory protein for DNA sequences. The final eluted 0.1-1.0% portion, for example, represents the most successful sequences, i.e., those that bind the most strongly to the target molecule. This portion is then collected. The presence and quantity of the desired circular oligomers in the collected fractions can be determined by UV absorbance. Alternatively, the presence and quantity of circular oligomers can be determined using radiolabeled oligomers and scintillation counting. Before further amplification and selection, this selected population is a subset of the original population of circular nucleic acid sequences having randomized sequences.

The selected population of circular sequences is then ready for amplification by the rolling circle technique. In the first step of the amplification method, the selected circular oligonucleotide sequences act as the circular templates. An oligonucleotide primer is added which is substantially complementary to part of the nonrandom linker sequence of the selected circular sequence, and the reaction is carried out as described previously. The linear product nucleotide multimer is cleaved by one of the previously described methods, such as by a restriction enzyme. The resultant oligomer, which is complementary to the starting precircle oligomer, is then cyclized. This creates a family of circular oligomers that is complementary to the original selected set.

This complementary set is in turn amplified by the rolling circle method, and the product is cleaved into oligomers and purified as described above. This resultant set of oligomers is cyclized. These cyclized oligomers are an amplified population of the original selected circular oligonucleotides. This population is then ready for further cycles of selection and amplification. Alternatively, the selected population of circular sequences can be linearized and amplified by standard cloning or PCR as described in Sambrook.

In principle, as many rounds of selection and amplification can be carried out as necessary. The success of a given round of selection can be judged by the percentage of the oligomer that elutes in late fractions from the affinity column, or the binding affinity of the population for the free target protein or receptor molecule as measured by standard methods. When most or all of the DNA or RNA, or analog thereof, binds tightly, then the selection process is typically complete. Preferably, the circular sequences undergo selection and amplification until a homogenous population of selected circular sequences having the same capacity to bind to and/or alter the function of a target molecule is obtained. Preferably, 2-25 rounds of amplification and selection is sufficient to generate a homogenous population and more preferably 3-13 rounds of amplification and selection.

From the selected population of circular sequences, the sequences of the individual oligonucleotides are then determined by standard methods such as Sanger sequencing or cloning. For example, in Sanger sequencing, the circles are linearized and sequenced by the method published in J. Sambrook et al., *Molecular Cloning*, 2nd ed.; Cold Spring Harbor Press, 1989, which is incorporated herein by reference. The sequencing information can be used to generate a consensus sequence for best binding by the method of A. D. Ellington et al., *Nature*, 346, 818 (1990), which is incorporated herein by reference. For example, position 100 may be found to be 98% T, and position 101, 40% G and 60% A. Some positions will be irrelevant to binding, and will remain randomized (about 25% of each of the four bases).

Individual selected sequences may be identified by the cloning method. In this method the circles are linearized, converted into duplex, and ligated into a convenient plasmid. This is used to transfect *E. coli*. Different clones of colonies will carry different sequences. Several colonies can be isolated and the corresponding DNA sequenced using techniques published in J. Sambrook et al., *Molecular Cloning*, 2nd ed.; Cold Spring Harbor Press, 1989, which is incorporated herein by reference.

To confirm that selected sequences bind, they can be independently synthesized by rolling circle or automated techniques, circularized, and tested for binding to the affinity column or to the free protein or other receptor. The various sequences can then also be tested for their ability to inhibit the protein or other function. An individual sequence which binds and inhibits the target molecule may be analyzed for its structure (as a drug lead), or it may be tested as a drug candidate itself by standard methods known to those of skill in the art. Anyone of the selected population of circular sequences can be identified and further amplified as all of the sequences in the selected population bind to and/or affect the function of the target molecule similarly. The preferred product is an individual selected circular nucleic acid sequence that inhibits the function of protein such as HIV reverse transcriptase.

An individual selected circular oligomer can also be selected for a property other than binding. For example, randomized sequences can be tested for their ability to catalyze a specific chemical reaction, such as the cleavage of a specific RNA or DNA sequence or a specific peptide bond. Other properties that could be selected include, for example, stability against degradation in biological fluids, or the ability to penetrate a cell membrane.

The amplification method for select sequences of the invention is novel and advantageous at least because: (1) it defines a novel subset of types of oligomers (i.e., circular with defined domains) that have potential advantages (binding affinity, stability, etc.) for use as a therapeutic agent; (2) it provides for large-scale production of the desired product; and (3) it defines a novel amplification procedure in the rounds of selection.

It is to be understood that the present invention also includes within its scope the following variations and embodiments of the above-described method. For example, circular molecules can be used in the selection process as described above while the amplification process can be carried out by linearizing and using PCR to amplify the desired strand. Recircularization would then follow. In another variation, partially double-stranded circular molecules, i.e., DNA dumbbells, are used. This alternative may be especially useful in inhibiting duplex DNA-binding proteins. In still another embodiment, the target molecule is a nucleic acid (RNA or DNA) rather than a peptide or protein.

Circular Nucleic Acid Sequences That Bind to and/or Modify the Function of a Target Molecule Circular nucleic acid sequences, such as DNA or RNA sequences, having a randomized domain are selected for binding to and/or for modifying the function of a target molecule. These circular sequences preferably contain 30–1500 nucleotides, and more preferably about 50–300 nucleotides and most preferably, 30–200. The circular sequences have a randomized sequence, i.e., domain, and a nonrandomized or constant sequence, i.e., domain. The random sequence is a particular length composed of the nucleic acid residues in a random order. A random sequence can consist of all five types of nucleic acid residues or a single residue or any combination of these different nucleic residues. The random sequence is preferably 5–1500 bases and more preferably 5–190 bases. The nonrandomized or constant sequence is a sequence that is specifically constructed to provide both a known site for primer binding and for cleavage. Preferably, the constant region is about 5–100 bases and more preferably about 8–40 bases in length.

Randomized nucleic acid sequences can be formed by any number of methods. Automated DNA synthesis can be used to generate multiple random sequences by providing mixtures of the different nucleic acid residues at each coupling step.

Nonnatural DNA bases carrying diverse functional groups could be incorporated into the random domain in yet another embodiment of the present invention. This can be done by enzymatic incorporation and would offer a greater range of structural or functional diversity. Examples of useful bases include, but are not limited to, phosphorothioate triphosphates, nucleotide triphosphates with other functional groups attached, or nucleotide triphosphates modified with linker precursors which will allow post-synthetic labelling or other modification.

A nonrandom or constant domain can also be designed and chemically synthesized by automated DNA synthesis. The constant domain contains at least one residue that can serve as a cleavage site. The selected method of cleavage as described previously will determine the choice of sequence for a cleavage site. Preferably, the cleavage site is a sequence that can be cleaved by a restriction enzyme and is not a sequence also found in the randomized sequence. Cleavage sequences for restriction enzymes are well known to those of skill in the art. The constant domain also contains a sequence that can serve as a primer binding site. The primer binding site sequence also is preferably not contained within the randomized sequence. The restriction enzyme cleavage sequence can also serve as the primer binding site. Alternatively, the primer binding site can be different than the restriction enzyme cleavage site.

The randomized sequence and constant region sequence are synthesized in one linear chain and cyclized by standard methods to form a population of circular sequences having different randomized sequences. A preferred method for forming the randomized sequence and the constant region is as follows. A linear precircle is chemically synthesized having three domains: left domain of known sequence (5–30 nucleotides); a randomized sequence of 5–190 nucleotides; and a right domain of known sequence (5–30 nucleotides). A phosphate is added to one end. When in circular form, the left and right domains will be adjacent to one another, with the right domain being 5' to the left domain. In the precircle linear form the left domain is at the 5' end, followed by the randomized sequence and then the right domain. The left and right domains are designed to create a restriction site upon joining of the two domains to create the known constant region. The restriction site is a sequence of 4 bases or longer and the corresponding restriction enzyme is chosen for its ability to cleave single-stranded DNA. The right domain serves as a primer binding site and is preferably 8–15 bases in length to allow for sufficient binding of the primer. Additional known DNA or RNA sequences can be added to the left and/or right domains as long as the restriction and primer binding sites are maintained. Once the linear precircle is synthesized, it is circularized as described previously and as shown in Example 5.

A number of different random sequences can be generated, all having a constant domain with the same sequence. For example, a population of circular DNA or RNA sequences can be formed by automated synthetic methods with up to $10^{13}$ different circular RNA or DNA randomized sequences. Preferably, the population contains about $1000–10^{13}$ different randomized DNA or RNA sequences and more preferably $10,000–10^{11}$ different sequences. The circular DNA or RNA sequences in the population are all preferably the same size. The population of circular RNA or DNA sequences having different randomized domains is then subjected to rounds of amplification and selection as described previously.

After multiple rounds of selection and amplification, a selected population of circular DNA or RNA sequences having the capacity to bind to and/or affect a target molecule as compared to the initial population of unselected circular sequences is obtained. The capacity of the selected population to bind to and/or affect a target molecule is assessed as described previously. Preferably, the selected population can bind to the target molecule such as a protein with about the same affinity as a natural substrate for an enzyme or an antigen for an antibody. This selected population contains a mixture of circular RNA or DNA sequences having different randomized domains but the same constant region domain and is homogeneous in the capacity to bind to and/or affect the function of a target molecule. The mixture preferably contains about 5–1000 different circular DNA or RNA sequences and have preferably about 5–30 different sequences.

From the selected population of circular DNA or RNA sequences, individual sequences can be identified and amplified by standard methods. These standard methods include sequencing by the Sanger method or by cloning. Anyone of the individual sequences in the selected population can be further amplified because they all are characterized by substantially the same functional capacity to bind to and/or affect the function of the target molecule. A preferred circular sequence is an individual sequence isolated from the population of selected circular sequences and that binds to the target molecule. The especially preferred individual circular DNA or RNA sequence is one that binds to a protein such as HIV reverse transcriptase with sufficient strength to inhibit the function of the protein in vitro or in vivo. The preferred individual circular sequences can serve as therapeutic agents such as an anticancer or antiviral drug or as a drug lead in a rational drug design program.

The following examples are offered to further illustrate the various specific and preferred embodiments and techniques. It should be understood, however, that many variations and modifications may be made while remaining within the scope of the present invention.

EXAMPLES

Example 1

Synthesis of a 34-nt DNA Oligomer

A linear 34-nucleotide (34-nt) precircle DNA oligonucleotide having the sequence (SEQ ID NO:1):

5'-pAAAGAAGAGG GAAGAAAGAA AAGGGGTGGA AAAG, was machine synthesized on a Pharmacia LKB Gene Assembler Plus using standard β-cyanoethyl phosphoramidite chemistry as disclosed in S. L. Beaucage et al., *Tetrahedron Lett.*, 22, 1859 (1981), which is incorporated herein by reference. This precircle template is complementary to the desired oligomer. The sequence of the desired oligonucleotide product is (SEQ ID NO:2):

5'-pTTTTCCACCC CTTTTCTTTC TTCCCTCTTC TTTC, which has an MnlI enzyme cleavage site at its end. Using this enzyme, a polymeric version of this oligomer, i.e., a multimer, can be cut into oligomers having this sequence. A ligation adaptor, 5'-TTTTCTTTCTT (SEQ ID NO:27), was also machine synthesized, as described above. This was also used as the primer oligomer.

The precircle template (100 nmol) was cyclized into the template circle (SEQ ID NO:3):

and a divalent metal in a manner analogous to that disclosed in G. Prakash et al., *J. Am. Chem. Soc.*, 114, 3523–3527 (1992), and E. Kanaya et al., *Biochemistry*, 25, 7423–7430 (1986). Gel electrophoresis was used to separate the circular product from starting material. This separation step was optional. Further experimental details of an analogous cyclization step are outlined in Example 5.

For the rolling circle synthesis of the desired oligonucleotide product, the template circle (10 μM), primer (10 μM), dATP (2 mM), dTTP (2 mM), and dGTP (2 mM) were dissolved in a buffer containing 34 mM tris(hydroxymethyl) aminomethane (Tris.HCl) (pH 7.4, obtained from Sigma Chemical Co., St. Louis, Mo.), 3.4 mM $MgCl_2$, 2.5 mM dithiothreitol, 25 μg/ml bovine serum albumin, and 20% polyethylene glycol 8000 (PEG 8000). The Klenow fragment of DNA Polymerase I (2 units, obtained from United States Biochemical, Cleveland, Ohio) was also added. The reaction was allowed to proceed for 1 hour at 0° C., and then for 6 hours at 37° C. Further experimental details of an analogous rolling circle synthesis step are outlined in Example 6. Gel electrophoresis of a small aliquot of this solution showed very light bands corresponding to the template and very dark slow bands corresponding to the nucleotide multimers produced. The sequence of these multimers is as follows (SEQ ID NO:4):

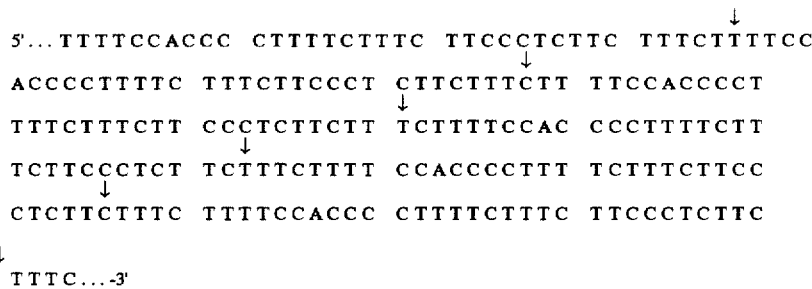

(arrows mark MnlI cleavage sites)

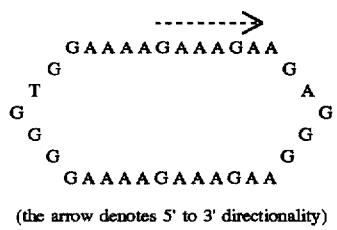

(the arrow denotes 5' to 3' directionality)

using the following method with the ligation adaptor to align the ends. The precircle template and ligation adaptor oligomers were placed in a 1-mL syringe in a programmable syringe pump. The oligomers were at 50 μM concentration. The syringe was connected by a tube to a 5-mL reaction vial. A reaction buffer, composed of 20 mM EDC, 20 mM mg C12, and 50 mM 2-(N-Morpholino) ethane-sulfonic acid (MES) buffer (obtained from Sigma Chemical Co., St. Louis, Mo.) was placed in the vial. The syringe pump was then used to deliver the adaptor to the reaction vial slowly (over a period of 24 hours at 4° C.). This method kept the effective concentrations very low, maximizing cyclization relative to dimerization. At the same time, it allowed the reaction to be carried out in a relatively small volume, making recovery of the product easier. Alternatively, the circular template can be constructed using BrCN/imidazole To cleave the product multimers into the desired oligonucleotide product, 10 units of MnlI restriction enzyme (available from New England Biolabs, Beverly, Mass.) can be added. Incubation at 37° C. results in cleavage of the multimers into a single product, which would be seen as a very dark band by gel electrophoresis. This dark band is the desired 34-base oligomer. Further experimental details for an analogous cleavage step are outlined in Example 7.

If desired, the oligomer could be further purified. Gel filtration should easily remove unreacted oligomers and the two proteins. If removal of the very small amount of circle template is desired, gel electrophoresis or affinity chromatography will accomplish this.

The oligonucleotide product can also be converted into circular form if desired, using the method described in G. Prakash et al., *J. Am. Chem. Soc.*, 114, 3523–3527 (1992), which is incorporated herein by reference. This method will work using the crude oligomer i.e., unpurified product, from the reaction. These 5'-phosphorylated circle precursors are hybridized with short complementary DNA templates, which bring the reactive 3'-hydroxyl and 5'-phosphate ends adjacent to one another. These ends are ligated using BrCN/imidazole/$Ni^{2+}$, in a manner analogous to the method described in G. Prakash et al. and E. Kanaya et al. It is worth noting that this second circle could be used as a template for rolling circle synthesis of the precircle template oligomer, eliminating the need for any machine synthesis in the long term.

Example 2

Synthesis of a Linear Oligomer of Sequence dT$_{12}$

The circular template used for the synthesis of the sequence 5'-pdTTTTTTTTTT TTp (SEQ ID NO:7) is (SEQ ID NO:5):

The precircle sequence used to synthesize this circular template is 5'-dCAAAAAAAA AAACAAAAAA AAAAAAp (SEQ ID NO:5). The primer/adaptor sequence is 5'-dTTTTGTTT. The circular template is constructed from the linear precircle and the adaptor using BrCN/imidazole under high dilution. Alternatively, the circular template can be constructed using 1-(3-dimethylaminopropyl)-3 ethylcarbodiimide HCl under the conditions described in Example 1.

For the rolling circle synthesis of the desired oligonucleotide product, only two triphosphates, dTTP and dGTP, are used following the conditions described in Example 1. Workup can be done by polyethylene glycol (PEG) precipitation. The product formed is the multimer 5' . . . GTTTTTTTT TTTGTTTTT TTTTTGTTT TTTTTTTTT . . . (SEQ ID NO:6). The pellet can be resuspended in a Maxam-Gilbert G buffer. This suspension is treated by the Maxam-Gilbert "G" reaction. The Maxam-Gilbert "G" reaction is described in J. Sambrook et al., *Molecular Cloning*, 2nd ed.; Cold Spring Harbor, 1989, Chapter 13, which is incorporated by reference. The resultant desired oligomer has the sequence 5'-pdTTTTTTTTTT TTp (SEQ ID NO:7).

Example 3

Synthesis of dAAGAAAGAAA AG

A schematic of the synthesis of the linear sequence 5'-pdAAGAAAGAAA AG (SEQ ID NO:8), is shown below in Scheme II. In this example, a partially self-complementary sequence was included in the circular template. No adapter was needed for cyclization because the molecule is self-complementary. The method for cyclization used is described in G. W. Ashley et al., *Biochemistry*, 30, 2927 (1991), which is incorporated herein by reference. The multimer was synthesized as described in Examples 1 and 5. The multimer product can be cleaved with BsmAI restriction enzyme, which removes the hairpins, leaving the desired product oligomer as the 5'-phosphate. Note that the product oligomer contains no restriction enzyme sequences.

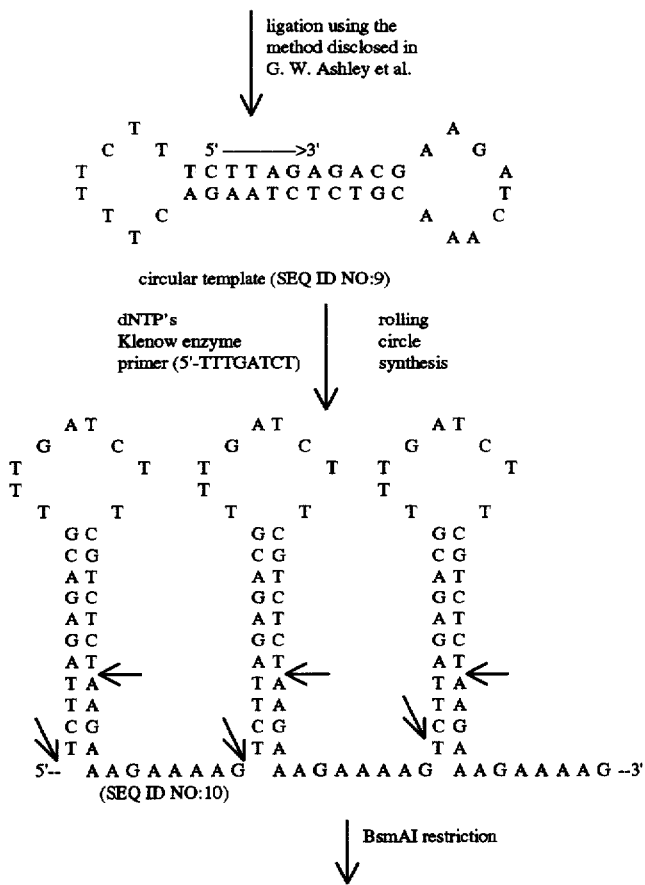

-continued
Scheme II

```
5' - pdAAGAAAGAAA AG
5'- pdAAGAAAGAAA AG
        5' - pdAAGAAAGAAA AG
```

Desired Oligomer (SEQ ID NO:11)
```
                    A T
                  G     C
              T             T           A T
              T                       G     C
          A T       T   T       T             T
        G     C    G C         T
       T           C G          T             T
       T           A T                 G C
          T     T  G C                 C G
          G C      A T                 A T
          C G      G C                 G C
          A T      A T                 A T
          G C      T                   G C
          A T      T                   A T
          G C      C                   T
          A T     5'-pdT                T
          T                             C
          T                            5'-pdT
          C
         5'-pdT
```
(SEQ ID NO:12)

Example 4

Synthesis of Additional Template

A circle very similar to that in Example 1 was constructed. In this example, the circular product was used as a template to produce more of the original template. A schematic illustration of this synthetic procedure is shown below in Scheme III.

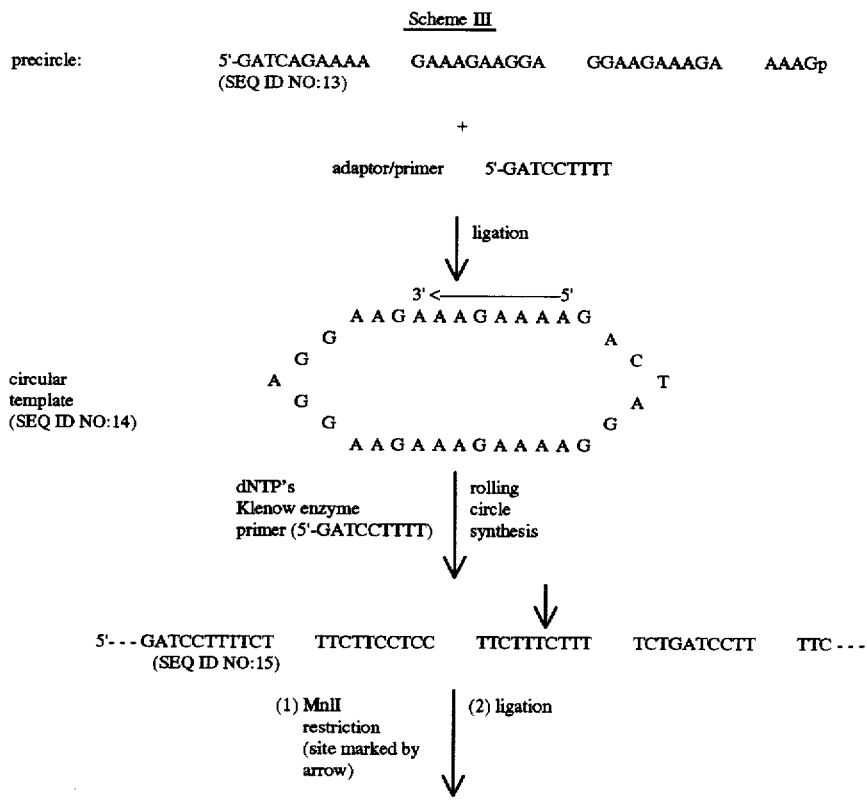

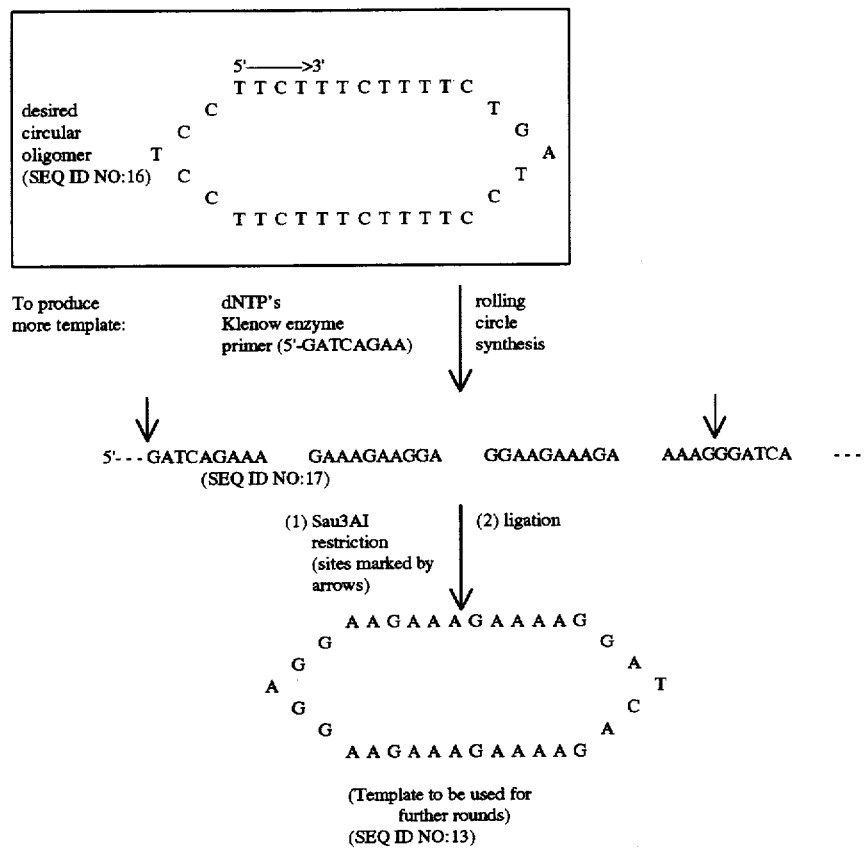

Example 5
Closure of Linear Oligomer Into Circular Form

DNA oligomers were synthesized on a Pharmacia LKB Gene Assembler Plus using standard β-cyanoethyl phosphoramidite chemistry as described in S. L. Beaucage et al., *Tetrahedron Lett.*, 22, 1859 (1981), which is incorporated herein by reference. The oligomer to be ligated (34-mer) had the sequence 5'-pAAAAGAAAGA AGGAGGAAGA AAGAAAAGGAT CAG (SEQ ID NO:18), and was 5' phosphorylated using Phosphate-On™ reagent (available from Cruachem, Sterling, Va.), whereas the shorter adaptor oligomer (8-mer) was left with hydroxyl termini. The template 34-mer was designed to include the single-stranded version of a double stranded restriction enzyme site such as that for Sau3AI (GATC). The adaptor 8-mer had the sequence 5'-TTTTCTCG, and was designed to be complementary to 4 bases at each terminus us of the template 34-mer, thus bringing the ends into proximity upon binding.

The 5'-phosphorylated oligomers were chemically ligated to produce primarily DNA circles using EDC. A typical preparative reaction contained up to 100 µM target and 100 µM adaptor in a 10 mL reaction containing 200 mM EDC, 20 mM MgCl$_2$, and 50 mM 2-(N-Morpholino) ethanesulfonic acid (MES) buffer (pH 6.1, obtained from Sigma Chemical Co., St. Louis, Mo.). To keep the concentration of target oligomer low enough to favor intramolecular reaction (circularization) over intermolecular reaction (multimerization), up to 1 µmol of prescribe oligomer dissolved in 1 mL of water was added to the other reagents (9 mL at 10/9 final concentration) at 4° C. over a period of 50 hours with stirring, using a syringe pump to carry out the addition. Reaction was continued for an additional 16–24 hours after addition was complete to promote maximal reaction.

Products were recovered by precipitation with 30 mL of ethanol in the presence of 100 µg of rabbit muscle glycogen carrier (Sigma Chemical Co., St. Louis, Mo.) and purified by preparative gel electrophoresis. Yields were calculated from absorbance measurements at 260 nm using extinction coefficients calculated by the nearest neighbor method.

Example 6
Synthesis of Single-Stranded Multimers Complementary to a Circular Template DNA circles synthesized as described in Example 5 were used to direct the primed synthesis of complementary multimers by the rolling circle method. The primer oligonucleotide was annealed to the template circle in a reaction consisting of 1 µL of 100 µM template circle, 1 µL of 100 µM primer, and 2 µL of 5× Klenow reaction buffer (335 mM Tris(hydroxymethyl)aminoethane)-HCl (pH 7.4), 34 mM MgCl$_2$, 25 mM dithiothreitol, and 250 µg/ml bovine serum albumin). This mixture was cooled from 25° C. to 4° C. over several hours and then either kept on ice or frozen for future use. The reaction mixture contained the annealing reaction (4 µL), 4 µL of 50% polyethylene glycol 8000 (PEG 8000), 1 µL mixed deoxyribonucleotide triphosphates (specifically this was a mixture of dATP, dTTP, dGTP, dCTP (sodium salts) each at 2 mM), and 1 µL of 2 U/µL Klenow fragment of DNA Polymerase I (United States Biochemical) and was assembled on ice. Synthesis was allowed to proceed for 1 hour at 0° C. and then for 6 hours at 37° C. Product multimers were recovered as a pellet by centrifugation at 10,000 rpm for 10 minutes at room temperature in a microcentrifuge.

Example 7

Enzymatic Cutting of Linear Multimers into Oligomers

Single-stranded multimers containing a restriction enzyme site were cleaved using the appropriate restriction enzyme at a temperature that allowed transient hybridization between restriction enzyme sites in either an intermolecular or intramolecular fashion to create a double stranded site. In the case of multimers containing the recognition site for Sau3Al, digestion of the multimers produced from the standard synthesis reactions described in Examples 5–7 was done as follows.

The PEG 8000 precipitate was dissolved in 10 µL reaction buffer (as recommended by the manufacturer of Sau3Al) containing 1 unit of Sau3Al (New England Biolabs, Beverly, Mass.). Digestion was allowed to proceed overnight at 25° C. and products were analyzed by electrophoresis on a 20% polyacrylamide, 8M urea denaturing gel. DNA was visualized by staining with methylene blue (Sigma Chemical Co.). The principal product had gel mobility identical to that of an authentic 34-mer, and had the sequence 5'-pdGATCCTTTTCT TTCTTCCTCC TTCTTTCTTT TCT (SEQ ID NO:19).

Example 8

Chemical Cleavage of Linear Multimers

This method can be used when the desired oligomer contains only one, two, or three different bases. An unused base is then incorporated into the multimer once at the end of every oligomer unit. For example, if the desired oligomer contains only C, A, and G bases, then the corresponding circular template will contain only the complementary G, T, and C bases; a single A base will be added at the site between the start and end of the desired sequence. The multimer transcript will consist of repeats of the desired sequence separated by a single T at each unit. Submitting this multimer to Maxam-Gilbert "T" reaction/cleavage conditions, as disclosed in J. Sambrook et al., *Molecular Cloning*, 2nd ed., Chapter 13; Cold Spring Harbor Press, 1989, incorporated herein by reference, results in cleavage of the chain at each T, with loss of the T base, and leaving the desired oligomers with phosphates on the ends.

Linear multimer can be isolated by pelleting from the transcription reaction as described above in Example 6. To confirm success of the rolling circle reaction, a small portion can be checked for length on an analytical scale by agarose gel electrophoresis, using markers of known length. Cleavage is then carried out on the isolated multimer, using standard Maxam-Gilbert-type conditions (scaling up as necessary for preparative amounts of DNA). The product oligomer can be isolated by ethanol precipitation.

For example, the sequence 5'-dCGAGAAAAGA AAGAAGGAGG AAGAAAGAAA AGA (SEQ ID NO:20) (a 33-mer) is the desired oligomer. The circular template then has the sequence (SEQ ID NO:21):

(the arrow denotes 5' to 3' directionality)

The rolling-circle reaction can be carried out as described above in Examples 1 and 6 (on larger scale), using the primer sequence 5'-dAAAGACG. This results in isolation of 50 mg of multimer after pelleting. Treatment of this product with hydrazine under Maxam-Gilbert conditions, followed by piperidine treatment, gives a reaction solution containing the desired monomer oligomers. Ethanol precipitation gives the isolated oligomer as desired. If necessary, this product can be further purified by reverse-phase, ion exchange, or gel filtration chromatography.

Example 9

Light-Induced Cleavage of Linear Multimers

In this method, light is used to induce multimer chain cleavage at a specially modified base, which occurs once at the end of every oligomer sequence in the multimer. This modified base contains a photolabile group, such as orthonitrobenzyl. When flashed with light, this group falls off and induces reaction to make the nucleoside anomeric bond itself labile to hydrolysis. Further piperidine treatment induces chain cleavage with loss of this base, as with Maxam-Gilbert methods.

This base may be a modified analog of one of the four natural bases, and in this case is coded for in the circular template by its natural complement. An example of a modified nucleotide base which can be made base-labile by irradiation with light is a pyrimidine (thymine or cytosine) which has been modified by an O-nitrobenzyloxycarbonyl-hydrazinoethyl group. UV irradiation induces loss of the O-nitrobenzyl group followed by decarboxylation, leaving the C5-hydrazinoethyl group. The hydrazine moiety reacts spontaneously with the pyrimidine base to which it is attached, making it labile to hydrolysis. Hydrolysis and multimer chain cleavage is carried out as described in Example 10.

Alternatively, this base is a nonnatural nucleotide which pairs with another nonnatural base. An example of such a nonnatural pair is the iso-C/iso-G pair described in J. Piccirilli et al., *Nature*, 343, 33 (1990), which is incorporated herein by reference. Use of such a nonnatural pair allows incorporation once per unit without placing requirements or restrictions on the use of the four natural bases in the desired sequence.

Example 10

Chemical Cleavage of Linear Multimers by Incorporation of a Nonnatural Activated Base The circular template is constructed to contain one nucleotide at the end of each coded oligonucleotide which is not contained within the desired oligomer sequence. This nucleotide codes for a nonnatural nucleotide which will be incorporated between each repeated oligomer sequence in the multimer.

This nonnatural nucleotide contains synthetic modifications which allow it to be cleaved selectively, leaving the desired DNA sequences untouched. Cleavage is carried out by addition of a chemical reagent to solution which reacts selectively with the nonnatural nucleotide base, phosphate, or ribose moiety.

In the case where the nonnatural activated nucleotide is a synthetic analog of a natural base, it will be coded for by the natural pair of that base. For example, if the nonnatural nucleotide is a synthetically modified deoxyadenosine, then it will be coded for by a thymidine in the circular template. In that case, the desired oligomer contains any combination of C, T, and G bases, but not A bases.

In the case where the nonnatural activated nucleotide does not pair with any of the natural bases, but instead pairs with a second nonnatural base, the activated nucleotide is coded for by the second nonnatural base in the template circle. For example, if the nonnatural activated base is a modified analog of deoxyisoguanosine, then it will be coded for by a deoxyisocytidine in the circular template. In that case, the desired oligomer may contain any of the four natural bases.

An example of a nonnatural activated nucleotide which is a synthetic analog of a natural base is described below. 8-allyldeoxyadenosine 5'-triphosphate (ADA) is incorporated into the linear multimer once at the end of each desired oligomer sequence. The ADA nucleotide is coded for by a thymidine in the template circle. The linear multimer is then cleaved in the following manner: an activating reagent is added to a solution of the multimer, which reacts with the three-carbon allyl moiety, producing an alkylating functional group at the end of the three-carbon chain. This functional group then spontaneously alkyates the N-7 position of the purine ADA base, leaving a positive charge on the base. It is now labile to hydrolysis, and the multimer is activated for chain cleavage. A second example of such a base is N-4-allyldeoxyadenosine, which will react in similar fashion.

Hydrolysis and multimer cleavage is carried out by the Maxam-Gilbert method: the activated multimer is dissolved in 10% aqueous piperidine and is heated to 90° C. for 30 min. The solution is frozen and lyophilized and is redissolved in water and dialyzed to remove the small products of cleavage from the desired oligomers. These product desired oligomers contain phosphates at both ends. If no phosphates are desired, they can be removed enzymatically.

An example of a nonnatural activated nucleotide which does not pair with any of the natural bases is 8-allyldeoxyisoguanosine (ADIG). It is cleaved by the same methods described in the preceding paragraph. Further examples include all purine structures which contain an N-5 and an N-7 moiety.

An example of an activating reagent which reacts with the allyl group is N-bromosuccinimide. A second example is molecular bromine ($Br_2$). A third example is an epoxidizing reagent.

A second example of a nonnatural activated nucleotide is (N4)-mercaptoacetyldeoxyadenosine, where the mercaptan is protected by a protecting group such as t-Butylthio. When this activated nucleotide is present in the multimer it can be made labile to hydrolysis by the following procedure: to a solution of the multimer is added sodium borohydride or dithio threitol to deprotect the mercaptan. The multimer is dialyzed to remove the small reaction products. An activating reagent is then added which reacts with the mercapto group to make it a good leaving group. The N7 of the purine then is spontaneously alkylated, making it labile to hydrolysis. Hydrolysis and multimer cleavage is then carried out as described above.

An example of an activating reagent for the mercaptan is acetic anhydride. This forms the acetylmercapto group, which is a good leaving group. A second example of an activating group is disodium chlorophosphate. A third example is 1-(3-dimethylaminopropyl)-3 ethylcarbodiimide HCl.

Example 11

Chemical Cleavage of Linear Multimers by Catalytic Alkylation of N7 of an Extra Purine This procedure requires no synthetically modified bases to be incorporated into the multimer. The circular template is constructed to contain one additional pyrimidine nucleotide (C is preferred) at the end of each coded oligonucleotide. After rolling circle synthesis, the multimer contains an extra purine nucleotide (G is preferred) in between each desired oligomer.

This extra purine can be made labile to hydrolysis in the following manner. An oligonucleotide modified with a thioether group is added to a solution of the multimer. This oligonucleotide is complementary to part of the desired oligomer sequence in the multimer. The thioether is thus brought into close proximity to the N7 group of the extra purine nucleotide. The proximity is controlled by careful choice of the sequence of the thioether-oligonucleotide and by the chemical structure of the chain carrying the thioether. After hybridization has occurred, an activating reagent is added to solution. This reagent alkylates the thioether to produce a reactive sulfenium group ($SR_3^+$). This group spontaneously alkylates the N7 group of the extra purine, and the product of the reaction is the alkylated purine in the multimer, and the thioether-oligonucleotide, which can then catalyze alkylation at another extra purine.

Hydrolysis and multimer chain cleavage is carried out as described in Example 10. Examples of activating reagents are dimethyl sulfate, S-adenosylmethionine, dimethylpyrocarbonate and trimethyl sulfur chloride. A further example of a thioether-oligonucleotide is a circular oligonucleotide modified with a thioether at the 5-position of a pyrimidine base. The preferred pyrimidine base is the same one that codes for the extra purine. The circular oligonucleotide contains the same sequence as the template circle.

Another example of this method is the case in which the thioether oligonucleotide is the same as the template circle. In this case, rolling circle synthesis is carried out and at the end of (or during) the reaction the chemical activating reagent is added to solution to make the multimer labile to hydrolysis.

Example 12

Use of a Randomized Circular Oligomer in Screening for Biological Binding, and Identification of a Circular Sequence as a Pharmaceutical Agent A pharmacological target molecule is selected for screening. This target will depend on the disease to be treated, and it is a target which, when strongly complexed at an active site, will result in a pharmacologically desirable effect. Examples of pharmacological target molecules and the expected result of binding include: binding of HIV reverse transcriptase or HIV tat protein for inhibition of the AIDS virus; binding of FK506 binding protein for activity as an immunosuppressant; binding of squalene synthase for a cholesterol lowering effect; binding of mutated p53 protein for an antitumor effect; binding of mutated ras protein for an antitumor effect; binding of the bcr-abl mutant protein for an antileukemic effect; binding of influenza coat proteins for an anti-influenza effect; binding opiate receptors for an analgesic effect; binding to a transcription repressor protein to enhance transcription of a specific gene; binding to the multidrug resistance protein to suppress resistance to anti-cancer drugs; binding to d-ala-d-ala to inhibit bacterial growth; binding to d-ala-d-lactate to inhibit growth of vancomycin-resistant enterococcus; binding of rhinovirus coat proteins for treatment of common cold; binding of resin to lower blood pressure; binding bcl-2 protein to induce apoptosis in cancer cells; binding of thrombin to inhibit clotting; and binding of NO-synthase to inhibit septic shock.

An affinity column is then prepared. The pharmacological target molecule is attached to a commercially available activated solid support using procedures suggested by the manufacturer. Usually this consists of simple mixing of the support with the molecule of choice.

A circular oligonucleotide pool is constructed, which is a series of same-size molecules that contain a randomized domain of 10–100 bases and a domain of known sequence of 8–40 bases in length. This pool is eluted down the affinity column under approximately physiological conditions of pH and ionic strength. Fractions are collected of this eluent. Nucleotide content can be measured by monitoring the eluent stream for absorbance at 260 nm, or individual fractions can be checked. The distribution of oligomers in the fractions will depend on each molecule's binding ability: early fractions will contain the majority of molecules, which have low affinity for the target molecule. Later fractions will contain fewer oligomer sequences which have better binding ability. The latest fractions which contain DNA can be collected; these will contain the best-binding subset of sequences. This last enriched pool will then be subjected to amplification using the rolling-circle procedure; alternatively, they can be linearized and a PCR procedure can be used. The amplified products are re-cyclized and subjected to further rounds of affinity selection and amplification. After 3–30 rounds the selected sequences will be enriched in only a few strong binding sequences. The successful molecules in this pool can be identified as to sequence and structure, and they can be tested for inhibition of the specific target's function in an in vitro or in vivo assay. The most inhibitory molecules may be used as pharmaceutical agents. Alternatively, the structure can be analyzed, and a synthetic molecule can be synthesized which mimics structurally the important parts of the selected oligonucleotide. This new synthetic molecule may be used as a pharmaceutical agent.

The successful subset of enriched circular molecules can be identified as to sequence in the following way: They are used as template circles in a rolling circle synthesis to produce a complementary set of multimers. A short linear primer is used (along with a DNA polymerase and the NTP's) to make a linear complement of the multimer set. A restriction enzyme is then used to cleave the set into short duplexes having sticky ends.

At the same time, a convenient plasmid vector is chosen which contains this same restriction site, and the short duplexes can be cloned using standard procedures. For example, the plasmid is also cleaved by this restriction enzyme to make a linear duplex with sticky ends. The set of short duplexes is mixed with this linear plasmid, and ligated with T4 DNA ligase. This will produce a set of new circular plasmids with the enriched circle sequences inserted. These can be transfected into *E. coli* according to standard procedures, plated and allowed to form colonies. Each colony can be identified by sequencing using standard procedures.

An alternative method for identifying sequence of the enriched circular oligomers is to linearize them with a restriction enzyme and sequence them directly using the Sanger dideoxy method. This will identify positions having strongly conserved bases and preferences in variable bases, and will show base positions that have no strong preference.

Example 13

Design and Construction of Partially Sequence-Randomized Circular Oligomers for Selection and Screening The total length of the circular oligomers will be 30–200 nucleotides. They will contain three domains: left domain of known sequence (5–30 nucleotides); a sequence-randomized domain of 5–190 nucleotides; and a right domain of known sequence (5–30 nucleotides). When in circular form, the left and right domains will be adjacent to one another, with the right domain being 5' to the left domain. In enzyme-linearized form, the left domain is at the 5'-end, followed by the random domain, and then the right domain. The initial synthesis is done using an automated synthesizer to construct a linear version of the oligomer with a phosphate on one end. Cyclization is carried out using the procedure described in Example 5. Alternatively, cyclization is carried out enzymatically, using T4 DNA ligase and a short adaptor oligomer which is complementary to the ends being joined, or using T4 RNA ligase without an adaptor.

To create the random domain using the synthesizer, two approaches can be taken. At the randomized positions, a fifth reagent bottle can be used which contains a mixture of the four phosphoramidites of the natural bases. A second approach is to use a synthesizer which can simultaneously draw reagents from more than one bottle at a time.

A randomized coupling step during DNA synthesis can be carried out with a completely sequence-random 1:1:1:1 mixture of the four phosphoramidites, or it can be any ratio of a mixture of two or more bases.

The design of the left and right domains requires the following features: the joining of the right and left domains creates a restriction enzyme site, and conversely, the cleavage of the circular oligomer with this enzyme creates a linear oligomer with the left domain on the 5' end and the right domain on the 3' end. The choice of restriction enzyme prefers the following features: the ability to cleave single-stranded DNa, and a recognition sequence of 5 bases or longer. One example is the enzyme BstN I, which recognizes the sequence 5'-CCAGG, cleaving it after the two C's, and with single strand cleaving activity. If a circular oligomer contains this sequence, the enzyme will cleave it, leaving the sequence 5'-AGG on the 5'-end, and the sequence 5'-GG on the 3'-end.

In linearized form, the right (3') domain must be able to serve as a primer binding site (for dideoxy sequencing), and so should be 8–15 bases in length to allow sufficient binding. The right and left domains should each be at least four bases in length to allow an adaptor oligomer to bind for the cyclization reaction. One skilled in the art can choose added bases which are required for these purposes in addition to the restriction sequence.

For rolling circle synthesis using a partially randomized circle, the sequence of the primer oligomer will be complementary to at least eight contiguous bases of the combined right and left domains.

Example 14

Effect of circle size on rolling circle DNA synthesis

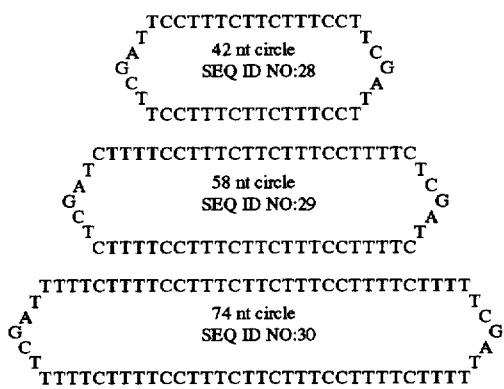

Successful rolling circle reactions using a 34 nucleotide circular template were described in Example 6. In order to investigate the effects of increasing size on the reaction, three larger circles 42-, 58-, and 74 nucleotides in length were tested. The primer sequence used was 5'-AGGAAAGAAGAAAGGA SEQ ID NO:31. Conditions for the reaction were as follows: 1.0 µM circle, 1–5 µM cold primer, 1.0 mM dNTP's, 2.5 units Klenow enzyme (USB), in a buffer containing 50 mM Tris.HCl (pH 7.5), 10 mM MgCl$_2$, 1 mM DTT, and 50 µg/mL BSA. The total reaction volume was 20 µL. The reaction was incubated for 3 hours at 37° C. and then quenched by addition of denaturing formamide loading buffer (80% formamide, 10 mM EDTA). The results were analyzed by polyacrylamide denaturing gel electrophoresis.

All three circles successfully extended the primer. Further, repetitive banding patterns appeared in the lanes corresponding to the RNA synthesized using each of the three circles. These banding patterns strongly indicate that the circles were indeed used as the RNA transcription template. The banding patterns did vary by circle size as predicted. Moreover, the lengths of the transcripts in all cases were about the same, in the general range of 1000–4000 nucleotides.

Thus, the rolling reaction was not sensitive to circle size over the range of about 28 to 74 nucleotides in size. It is remarkable that a circle as small as 28 nucleotides, which is considerably smaller than the polymerase itself, behaved as a good template.

Example 15

Comparison of rolling circle reactions on small synthetic circles and on single-stranded phage φX174

Standard rolling circle conditions as given in Example 6 were used to elongate primers complementary to the above three circles (42–74 bases in length) and to a single-stranded, 5386 nucleotide-long phage. The primer for the synthetic circles was 5'-AGGAAAGAAGAAAGGA SEQ ID NO:31, and that for the phage was 5'TGTTAACTTCT-GCGTCAT SEQ ID NO:32. Both primers were radiolabeled, and the reactions were run as before, using a 1 µM concentration of circle. The results were analyzed by 1% agarose gel electrophoresis, and a 1-kB marker ladder was used to evaluate sizes. Results of the experiment showed that the primers were successfully elongated in all four cases, and the products have fairly wide size distributions.

The reactions using the three synthetic circles as templates gave products with banding indicating a multimeric sequence. The lengths ranged generally from 500 to 2000 nucleotides, indicating the presence of multimers that are ~25–50 monomer units in length. The experiment using φX174 gave different results. The lengths of the products fell in the ~2000–8000 nucleotide range. Therefore, the products contained only ~0.5 to 1.5 monomers, since the template circle was ~5 kB in size.

The results establish that many more useful monomers can be produced from small synthetic circles than can be produced from a much larger naturally occurring circle. Further, the larger circle did not "roll" successively, that is, it did not progress substantially more than once around the circle. Possibly the duplex being synthesized inhibits the further progression of the polymerase after the first time around, as has been reported in the literature. The small circles are short enough that any duplex being formed is strained by the curvature, and tends to unwind spontaneously as synthesis progresses.

Example 16

Construction of a DNA circle containing a randomized domain

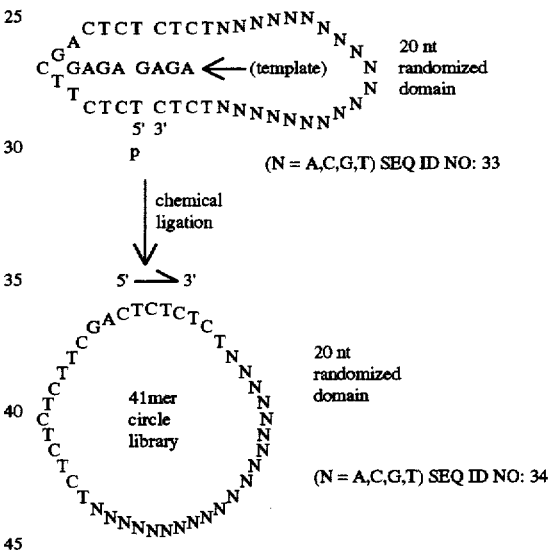

A 41-nucleotide DNA circle was constructed to have a 20-nt randomized domain as shown. The circle precursor contained a 5' phosphate and was designed to form a triple helical complex with a short purine-rich template as shown. The randomized part of the precursor was made using one bottle of mixed A, T, C, G phosphoramidites on the DNA synthesizer. Precursor (50 µM) and template oligomers (55 µM) were incubated for 7.5 hours at room temperature in a buffer containing 100 mM NiCl$_2$, 200 mM imidazole.HCL (pH 7.0), and 125 mM BrCN. The circular product depicted above was produced by the reaction and was isolated by preparative denaturing PAGE.

This product with its 20-nucleotide randomized domain represents a mixture of ~$10^{12}$ different circular DNA sequences. This mixture, or library, is suitable for subsequent selection/amplification experiments.

Example 17

Confirming the Multimer Sequence in Rolling Circle DNA Synthesis

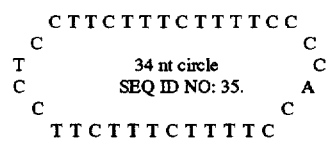

The above circle was used as template in a standard rolling circle reaction under conditions described in Example 6 above. The primer used was 5'-AAGAAAGAAAAG SEQ ID NO:36. After the reaction, the products were analyzed by electrophoresis on a 1% agarose gel and visualized by staining. One of the dark bands, having a length of approximately 1000 nucleotides, was excised and the DNA recovered from the gel by simple elution. This DNA was then sequenced using Sanger dideoxy methods, using a primer of sequence 5'-pTTTCTTCCTCCTTCTTTCTTTTCCCCACCTTTTC SEQ ID NO:37 (which corresponds to the precursor of the circle used as template). The sequencing results indicate that this approximately 1000-nucleotide length DNA was a multimer of the expected repeating monomer sequence. There was a minor background of other sequences, but it was clear that the major product was a multimer of the expected repeating monomer.

Example 18

Small Synthetic DNA Circles Act As Efficient Templates for RNA Synthesis

Small synthetic DNA circles can act as templates for RNA synthesis in addition to DNA synthesis. The following DNA circle was used as an efficient template for RNA synthesis:

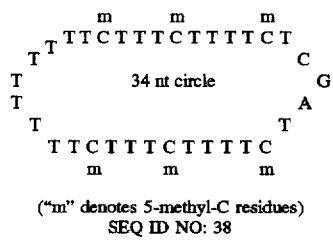

("m" denotes 5-methyl-C residues)
SEQ ID NO: 38

Standard runoff transcription reactions using linear DNA template with a T7 RNA Polymerase promoter at the 5'-end of the sequence were carried out as described in Milligan et al., *Nucleic Acids Res.*, 15:8783 (1987). In some reactions the circular template depicted above was added, and extra long bands were found in some of the reaction tubes containing the circular template in addition to the linear template.

A control experiment was then carried out in which the linear runoff template was not included in the reaction tubes. Long RNA molecules were produced in the presence of circular template alone. This was especially surprising since the circular template did not contain any known promoter sequences.

Transcription reactions were performed using $\alpha$-$^{32}$P-dUTP as a limiting nucleotide to allow efficient labeling of the RNA being synthesized. In the reactions containing circular template, an apparent repeating banding pattern was found, and most of the products found were longer than what a 15% gel could resolve. Further, the intensity of the bands resulting from the use of the circular template alone were approximately as strong as those produced by the linear promoter template alone. These results indicated that the two transcription reactions were roughly equivalent in efficiency.

Example 19

Rolling circle RNA synthesis does not require a promoter 41-mer DNA circles containing a 20-nucleotide variable sequence domain were synthesized as described in Example 1. The 20-nucleotide variable sequence domain contained runs of $T_{20}$, $C_{20}$, $A_{20}$, and $G_{20}$. Some of the circles contained an optimized T7 RNA polymerase promoter: $N_{20}$=5'-CCCTATAGTG AGTCGTATTA SEQ ID NO:39. These 41-mer circles were used to synthesize single-stranded multimers using the the following conditions: 25 mM Tris-HCl, pH 8.1; 20 mM NaCl; 15 mM MgCl$_2$; 0.4 mM spermine4HCl; 100 µg/mL Acetylated BSA; 10 mM dithiothreitol; 12.5 U/mL RNase inhibitor (Promega); 0.5 mM each rATP, rGTP, rCTP; 0.27 µCi $\alpha$-$^{32}$P rUTP; 1 µM template circle (AG2C1); 50 U T7 RNA Polymerase (New England Biolabs). Results of these rolling-circle reactions showed that circles containing $T_{20}$ and $C_{20}$ domains gave long RNAs; however, those with $A_{20}$ and $G_{20}$ domains did not. It is likely that long A runs inhibit transcriptional elongation. This finding, in fact, has been reported previously in the literature. J. Tomizawa and H. Masukata, *Cell* 51:623 (1987). The poor elongation with the $G_{20}$ run is likely due to the circle forming aggregates because of the G-rich sequence.

Finally, the data show that when a T7 promoter was present in the circle, only short RNAs were produced. This indicates that for some reason the rolling, or progression of the polymerase, was retarded by the promoter sequence. Thus, the rolling circle reaction of the present invention preferably works with circular templates that do not contain polymerase promoters. This ability to work better in the absence of polymerase promoters, along with the unusually small circle sizes, makes the process of the present invention different from natural transcription of circular templates. Further, the circular templates of the present invention encode only the RNA of interest and not extraneous sequences that are normally found when sequences are transcribed from plasmids.

Example 20

Use of different RNA polymerase enzymes for rolling circle RNA synthesis

Four separate enzymes were tested for their ability to carry out transcription on 34-mer circular templates. The enzymes used were T7 (New England Biolabs), T3 (Promega), and SP6 (Gibco BRL) RNA polymerases derived from phages, and *E. coli* RNA Polymerase (Boehringer Mannheim). The working concentrations of the T7, T3 and SP6 polymerases were 2 U/µl and the working concentration for *E. coli* RNA Polymerase was 0.3 U/µl. The synthesis reactions were performed under the conditions set forth in Example 19 above. No auxiliary proteins (such as DNA unwinding protein, cisA protein, or rep protein) were added to the reactions. Products were examined by both polyacrylamide and agarose gel electrophoresis, and were internally radiolabeled using limiting $\alpha$-$^{32}$P-dUTP.

All four enzymes worked well at rolling transcription. The only observable difference in efficiency among the different enzymes was that the *E. coli* RNA Polymerase gave somewhat longer RNA products than the other three enzymes.

Example 21

Rolling circle RNA synthesis in an extract from eukaryotic cells

Eukaryotic RNA polymerases were also tested for their ability to carry out transcription on circular templates. A commercially available nuclear extract from Drosophila (Promega) was added to reactions both containing and lacking a 34-mer template under the following recommended transcription conditions 7.5 mM HEPES buffer, pH 7.6; 60 mM potassium glutamate; 3.75 mM MgCl$_2$; 0.03 mM EDTA; 1.5 mM DTT; 3% glycerol; 0.5 mM each rATP, rCTP, rGTP; and 0.06–0.02 mM rUTP. The concentration of circular template was 3 μM. When no circular DNA templates were added, the extract can by itself give a small amount of new radiolabeled RNA. However, when a 34-nucleotide circle was present, a much larger amount of RNA was observed. These RNA molecules were too long to be resolved by polyacrylamide gel electrophoresis. Two experiments were performed to confirm that the RNA transcription was due to rolling transcription. First, a control reaction was performed using the linear precursor to the circle, and the result was very little RNA. This suggested that the circular structure was essential for the RNA synthesis. Second, the concentration of UTP was successively lowered, producing observable, regular banding patterns indicative of repetitive sequences. This result also suggested that the circular template was being used in rolling transcription. Thus, RNA polymerases from higher organisms can use small circles as templates. It is therefore likely that if such circles are delivered into living cells, the circles will act as templates for the production of RNA.

Example 22

Initiation sites and sequences of RNA multimers

The circle shown in Example 18 was used as a template in a series of rolling circle transcription reactions in which varying amounts of rUTP were added. The conditions for the reactions were as follows: 25 mM Tris-HCl, pH 8.1; 20 mM NaCl; 15 mM MgCl$_2$; 0.4 mM spermine4HCl; 100 μg/mL Acetylated BSA; 10 mM dithiothreitol; 12.5 U/mL RNase inhibitor (Promega); 0.5 mM each rATP, rGTP, rCTP; 0.27 μCi α-$^{32}$P rUTP; 1 μM template circle (AG2C1); 50 U T7 RNA Polymerase (New England Biolabs). The concentration of rUTP was varied in the series of reactions from 0 to 60 mM. The reactions were carried out in a reaction volume of 15 μL for 1.5 hours at 37° C.

Polyacrylamide gel analysis for the products showed that as the limiting nucleotide (rUTP) decreased, regular repeating banding patterns became evident on the autoradiogram. The repeating unit corresponded to 34 nucleotides, the length of the template. Closer examination showed that the dark bands appeared largely at sites where a C residue was present in the circle. Thus, initiation of transcription is occurring primarily at C template residues, using rGTP as the first nucleotide in the transcribed RNA strand.

Subsequent experiments were performed with circles containing 28 T's and only one C nucleotide. These experiments showed that it was also possible to initiate transcription at a T (using a rATP as the first nucleotide). In general, a circle is likely to require at least a short pyrimidine-rich domain so that transcription can initiate.

The above results also provide strong evidence that the circle is successfully serving as the template for a desired RNA multimer. All other circles have shown similar banding patterns (although with different sequences and lengths) when limiting UTP is present. As a second check on this we isolated a longer band about 150 nucleotides in length from a transcription reaction, and then treated it with RNase T1. Results showed bands as predicted from the expected nucleotide selectivity of this enzyme.

Example 23

Circles encoding repeating stem-loop antisense RNAs

It has previously been shown (E. D'Souza and E. Kool, *J. Biomolecular Structure and Dynamics*, 10:141 (1992)) that stem-loop DNA structures can bind tightly to single-stranded DNA targets by triplex formation. Similar binding of single-stranded RNA targets is possible by use of stem-loop RNA structures. These stem-loops bind tightly to a disease-related mRNA or viral RNA and inhibits mRNA splicing, mRNA translation, or viral replication. A 53-mer circle containing a binding domain that encodes a binding sequence that can bind to HIV-1 gag gene near the start codon, and a structural domain that encodes a stem-loop sequence is constructed as shown below. When transcribed by the rolling circle method it produces a repeating sequence which folds into multiple stem-loop structures. These stem-loop structures then bind tightly to a targeted RNA, inhibiting gag translation in vitro. When added to HIV-1 infected cells it enters the cell by endocytosis, is transported to the nucleus, and is transcribed by the rolling circle process. The resulting stem-loop multimer inhibits viral replication by binding multiple HIV RNAs at the gag gene site.

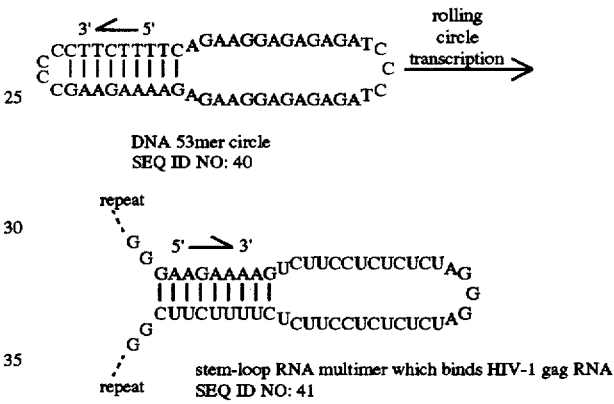

Alternatively, the 53 mer circle encodes a repeating RNA multimer, shown below, which folds into stem-loop structures which bind bcr-abl mRNA from the Philadelphia chromosome mutation leading to chronic myeloid leukemia. The stem-loops bind a sequence directly at the L6-type junction, thus causing inhibition of translation of this mRNA and inhibiting growth of the leukemic cells.

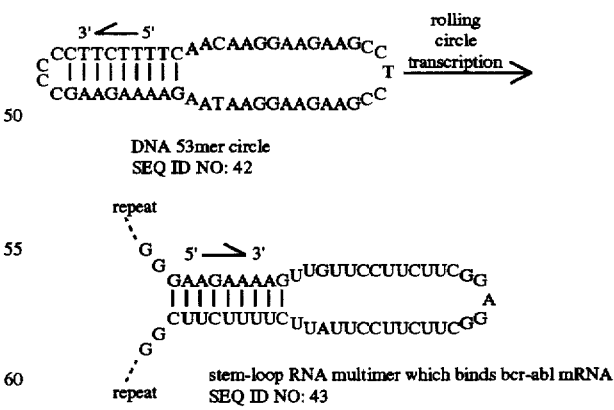

Example 24

Circles encoding RNA hairpin decoy sequences

A circle is constructed which encodes multimer RNAs that fold into repeating hairpin structures. Hairpin structures are double helical regions formed by base pairing between adjacent (inverted) complementary sequences in a single strand of RNA or DNA. These hairpins correspond to known binding sites for viral proteins that are important for viral replication. This binding to the multimer hairpins causes these proteins to be sequestered, rendering them unable to activate viral replication efficiently. Examples of known proteins in HIV-1 that could be bound by this method are the tat protein, which normally binds TAR RNA, and rev protein, which normally binds RRE RNA. U. Vaishnav and F. Wong-Staal, *Ann. Rev. Biochem.*, 60, 577 (1991).

A specific sequence is shown below. This 45 mer circle encodes repeating multimers of RNA that fold into hairpins capable of binding the HIV-1 rev protein tightly. It contains a binding site capable of binding the HIV-1 rev protein, and a structural domain that encodes a hairpin sequence. Addition of these DNA circles to HIV-1-infected cells leads to inhibition of viral replication.

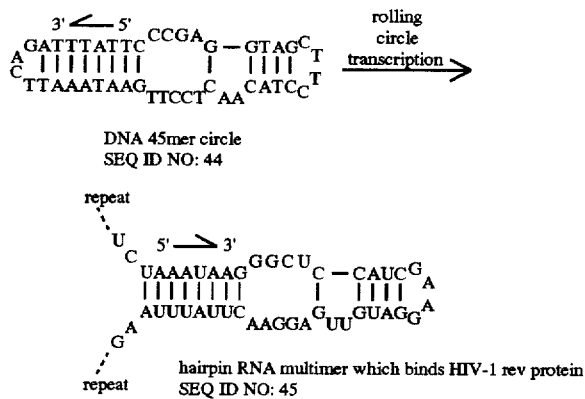

Example 25

Circles encoding ribozymes which cleave RNA

Another way to inhibit translation of specific genes is to generate short RNA ribozymes which cleave specific RNA sequences in a given gene, thus leading to gene inactivation. Hammerhead-type and hairpin-type ribozymes can be constructed from short RNAs of about 14–75 nucleotides in length. Circular DNAs are constructed for encoding specific ribozyme sequences. These circles contain a binding sequence that can bind a target in RNA, and a structural domain that encodes the ribozyme. A circle can encode a repeating ribozyme multimer which remains concatenated but still folds into active ribozymes. Alternatively, a circle can encode both a ribozyme and its cleavage site. In this second case the multimeric ribozyme first cleaves itself into monomer-length ribozymes; then it goes on to cleave the target mRNA or vital RNA in trans.

For example a 49 mer DNA circle is made that encodes a hammerhead-type ribozyme and its cleavage site which corresponds to the abnormal junction of the Philadelphia chromosome bcr-abl mRNA. When the DNA circle is added to CML cells it is transcribed by the cellular machinery into a multimeric RNA. This multimer first cleaves itself successively into shorter units (as short as monomer), and these shorter units cleave the mutant RNA. Thus, the circular DNA assists in inhibiting leukemic cell growth.

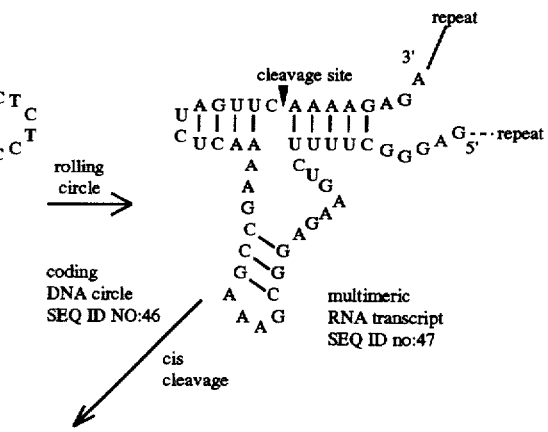

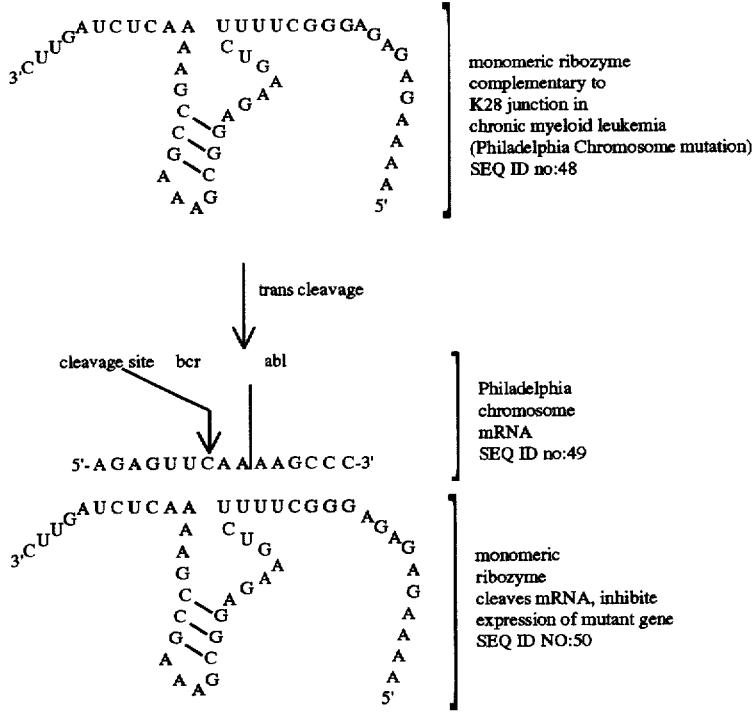

All patents, patent documents and publications cited above are incorporated by reference herein. The foregoing detailed description has been given for clarity of understanding only and no unnecessary limitations are to be understood thereforem. The invention is not limited to the exact details shown and described, for obvious modifications will occur to those skilled in the art.

What is claimed is:

1. A method for synthesizing a selected oligonucleotide having well-defined ends comprising:
   (a) annealing an effective amount of an oligonucleotide primer to a single-stranded circular template to yield a primed circular template, wherein the single-stranded circular template comprises (i) at least one copy of a nucleotide sequence complementary to the sequence of the selected oligonucleotide and (ii) at least one nucleotide effective to produce a cleavage site in the oligonucleotide multimer;
   (b) combining the primed circular template with an effective amount of at least two types of nucleotide triphosphates and an effective amount of a polymerase enzyme without the addition of auxiliary proteins to yield a single-stranded oligonucleotide multimer complementary to the circular oligonucleotide template, wherein the oligonucleotide multimer comprises multiple copies of the selected oligonucleotide; and
   (c) cleaving the oligonucleotide multimer at the cleavage site to produce the selected oligonucleotide having well-defined ends.

2. The method of claim 1 wherein the step of cleaving the oligonucleotide multimer occurs after the oligonucleotide multimer is completely formed.

3. The method of claim 1 wherein the step of cleaving the oligonucleotide multimer occurs as the oligonucleotide multimer is being formed.

4. The method of claim 1 wherein the step of cleaving the oligonucleotide multimer includes cleaving the oligonucleotide multimer with a restriction enzyme.

5. The method of claim 1 wherein the cleavage site comprises a cleavable natural nucleotide not present in the selected oligonucleotide sequence, and the step of cleaving the oligonucleotide multimer includes chemically cleaving the oligonucleotide multimer at the cleavable natural nucleotide.

6. The method of claim 1 wherein the cleavage site includes a cleavable modified nucleotide.

7. The method of claim 6 wherein the modified nucleotide includes a photolabile group, and the step of cleaving the oligonucleotide multimer includes cleaving the photolabile group with light.

8. The method of claim 1 wherein each of the circular oligonucleotide template, the oligonucleotide primer, and the nucleotide multimer is single-stranded.

9. The method of claim 8 wherein the single-stranded oligonucleotide primer is a DNA oligomer.

10. The method of claim 9 wherein the polymerase enzyme is selected from the group consisting of DNA Polymerase I, Klenow fragment of DNA Polymerase I, T4 DNA Polymerase, T7 DNA Polymerase, Taq Polymerase, and AMV Reverse Transcriptase, and homologs of each having at least about 80% homology to said polymerase enzyme.

11. The method of claim 10 wherein the polymerase enzyme is a Klenow fragment of DNA Polymerase I.

12. The method of claim 8 wherein the single-stranded oligonucleotide primer is an RNA oligomer.

13. The method of claim 12 wherein the polymerase enzyme is selected from the group consisting of T7 RNA Polymerase, T4 RNA Polymerase, SP6 RNA Polymerase, RNA Polymerase II, RNA Polymerase III, T3 RNA Polymerase, E. coli RNA Polymerase and homologs thereof having at least about 80% homology.

14. The method of claim 8 wherein the single-stranded oligonucleotide primer is a synthetically modified analog of DNA or RNA.

15. The method of claim 8 wherein the single-stranded oligonucleotide primer comprises about 4–50 nucleotides.

16. The method of claim 8 wherein the single-stranded oligonucleotide circular template comprises about 15–1500 nucleotides.

17. The method of claim 1 wherein the primer and circular template are provided in an effective catalytic amount.

18. The method of claim 1 wherein the primer is provided in an amount of about 0.1–100 moles per mole of circular template.

19. The method of claim 1 wherein the nucleotide triphosphates are provided in an amount of about $50-10^7$ moles per mole of circular template.

20. The method of claim 1 wherein the circular oligonucleotide template is prepared by a process comprising the steps of:
    (a) hybridizing each end of a linear precursor oligonucleotide to a single positioning oligonucleotide having a 5' nucleotide sequence complementary to a portion of the sequence comprising the 3' end of the linear precursor oligonucleotide and a 3' nucleotide sequence complementary to a portion of the sequence comprising the 5' end of the linear precursor oligonucleotide, to yield an open oligonucleotide circle wherein the 5' end and the 3' end of the open circle are positioned so as to abut each other; and
    (b) joining the 5' end and the 3' end of the open oligonucleotide circle to yield a circular oligonucleotide template.

21. The method of claim 1 wherein the single-stranded circular oligonucleotide template comprises about 15–1500 nucleotides.

22. The method of claim 21 wherein the single-stranded circular oligonucleotide template comprises about 24–500 nucleotides.

23. The method of claim 22 wherein the single-stranded circular oligonucleotide template comprises about 30–150 nucleotides.

24. The method of claim 1 wherein the selected oligonucleotide comprises about 4–1500 nucleotides.

25. The method of claim 1 wherein the oligonucleotide multimer is about 4–4000 times the length of a linearized circular oligonucleotide template.

26. The method of claim 1 wherein the oligonucleotide multimer has about 60 to 5,000,000 nucleotides.

27. The method of claim 26 wherein the oligonucleotide multimer has about 500–100,000 nucleotides.

28. The method of claim 1 wherein the oligonucleotide multimer has 5–100,000 copies of the selected oligonucleotide.

29. The method of claim 1 wherein the single-stranded circular template consists of the at least one copy of a nucleotide sequence complementary to the sequence of the selected oligonucleotide and the at least one nucleotide effective to produce a cleavage site on the oligonucleotide multimer.

30. The method of claim 29 wherein the single-stranded circular template consists of a single copy of a nucleotide sequence complementary to the selected oligonucleotide sequence and the at least one nucleotide effective to produce a cleavage site on the oligonucleotide multimer.

31. The method of claim 1 or 29 wherein the nucleotide sequence complementary to the sequence of the selected oligonucleotide comprises the at least one nucleotide effective to produce a cleavage site on the oligonucleotide multimer.

32. The method of claim 1 wherein the step of cleaving further includes annealing to the oligonucleotide multimer an adaptor oligonucleotide complementary to a region of the oligonucleotide multimer to produce a cleavage site on the oligonucleotide multimer cleaved by a restriction enzyme.

33. The method of claim 32 wherein the restriction enzyme is a Type II restriction enzyme, and wherein the adaptor oligonucleotide comprises a double-stranded region comprising a recognition site for the Type II restriction enzyme.

34. The method of claim 4 wherein the step of cleaving further includes annealing to the oligonucleotide multimer an adaptor oligonucleotide having a sequence complementary to a region of the oligonucleotide multimer comprising the cleavage site to yield a double-stranded site cleaved by the restriction enzyme.

35. The method of claim 34 wherein the restriction enzyme is a Type II restriction enzyme, and wherein the adaptor oligonucleotide comprises a double-stranded region comprising a recognition site for the Type II restriction enzyme.

36. The method of claim 35 wherein the double-stranded region of the adaptor oligonucleotide is formed by a DNA hairpin.

37. The method of claim 4 wherein the restriction enzyme cleaves the oligonucleotide multimer at a double-stranded site comprising the cleavage site, which double-stranded site is formed by interstrand or intrastrand base-pairing of the oligonucleotide multimer.

38. The method of claim 37 wherein the double-stranded site is a DNA hairpin formed by intrastrand base-pairing of the oligonucleotide multimer, and wherein the step of cleaving the oligonucleotide multimer includes excising the hairpins from the oligonucleotide multimer with a Type II restriction enzyme.

39. The method of claim 4 wherein the restriction enzyme cleaves the oligonucleotide multimer at a single-stranded site comprising the cleavage site.

40. The method of claim 4 wherein the selected oligonucleotide comprises at least one nucleotide effective to produce a cleavage site on the oligonucleotide multimer.

41. The method of claim 40 further comprising contacting the the selected oligonucleotide with a nuclease or restriction enzyme to remove the at least one cleavage site nucleotide.

42. The method of claim 41 wherein the nuclease used to remove the at least one cleavage site nucleotide from the selected oligonucleotide is an exonuclease.

43. The method of claim 1 wherein the step of cleaving the oligonucleotide multimer comprises cleaving the oligonucleotide multimer at the cleavage site with an endonuclease.

44. The method of claim 5 wherein the cleavable natural nucleotide occurs once between each oligonucleotide in the oligonucleotide multimer.

45. The method of claim 26 wherein the positioning oligonucleotide is the oligonucleotide primer.

46. The method of claim 1 wherein the single-stranded circular template contains no nucleotides other than i) the at least one copy of a nucleotide sequence complementary to the sequence of the selected oligonucleotide, and (ii) the at least one nucleotide effective to produce a cleavage site in the oligonucleotide multimer.

47. The method of claim 1 wherein the effective amount of the oligonucleotide primer is a catalytic quantity.

* * * * *

UNITED STATES PATENT AND TRADEMARK OFFICE
CERTIFICATE OF CORRECTION

PATENT NO. : 5,714,320
DATED : February 3, 1998
INVENTOR(S) : Eric T. Kool

It is certified that error appears in the above-identified patent and that said Letters Patent is hereby corrected as shown below:

Col. 1, line 53, delete "in vive" and insert --in vivo--;

Col. 10, line 25, delete "5-" and insert --5'--;

Col. 11, line 30, delete "adapter directed" and insert --adapter-directed--;

Col. 11, lines 38-39, delete "oligonucleotides" and insert --oligonucleotide--;

Col. 11, line 44, delete "a complex" and insert --an open oligonucleotide circle--;

Col. 11, line 45, delete "precircle" and insert --precursor--;

Col. 16, line 47, delete "cl" and insert --d--;

Col. 25, line 5, insert --+-- after box outlining sequence for SEQ ID NO:11;

Col. 27, line 20, delete "GATCAGAAA" and insert --GATCAGAAAA--;

Col. 28, line 20, delete "AAAGGGATCA" and insert --AAAGGATCA--;

Col. 27, line 54, delete "us";

Col. 42, line 24, delete "vital" and insert --viral--;

Col. 43, line 18, arrow connected to "cleavage site" should be pointed between "C" and "A";

UNITED STATES PATENT AND TRADEMARK OFFICE
CERTIFICATE OF CORRECTION

PATENT NO. : 5,714,320
DATED : February 3, 1998
INVENTOR(S) : Eric T. Kool

It is certified that error appears in the above-identified patent and that said Letters Patent is hereby corrected as shown below:

Col. 43, line 25, delete "inhibite" and insert –inhibits–;

Col. 64, line 22, insert –to said polymerase enzyme– after "homology"; and

Col. 66, line 33, delete "26" and insert –20–.

Signed and Sealed this

Seventeenth Day of August, 1999

Attest:

Attesting Officer

Q. TODD DICKINSON

Acting Commissioner of Patents and Trademarks